US008492372B2

(12) United States Patent  (10) Patent No.: US 8,492,372 B2
Sonesson et al.  (45) Date of Patent: Jul. 23, 2013

(54) MODULATORS OF DOPAMINE NEUROTRANSMISSION

(75) Inventors: Clas Sonesson, Billdal (SE); Peder Svensson, Göteborg (SE); Mikael Andersson, Vintrosa (SE)

(73) Assignee: Integrated Research Laboratories Sweden AB, Gothenburg (SE)

( * ) Notice: Subject to any disclaimer, the term of this patent is extended or adjusted under 35 U.S.C. 154(b) by 194 days.

(21) Appl. No.: 12/990,043

(22) PCT Filed: Apr. 28, 2009

(86) PCT No.: PCT/EP2009/055140
§ 371 (c)(1),
(2), (4) Date: Dec. 20, 2010

(87) PCT Pub. No.: WO2009/133110
PCT Pub. Date: Nov. 5, 2009

(65) Prior Publication Data
US 2011/0112065 A1  May 12, 2011

Related U.S. Application Data

(60) Provisional application No. 61/049,057, filed on Apr. 30, 2008.

(30) Foreign Application Priority Data

Apr. 29, 2008 (DK) .................................. 2008 00600

(51) Int. Cl.
A61K 31/357 (2006.01)
A61K 31/4025 (2006.01)
A61K 31/397 (2006.01)
A61K 31/4433 (2006.01)
C07D 319/08 (2006.01)
C07D 405/12 (2006.01)

(52) U.S. Cl.
USPC ...... 514/210.19; 514/319; 514/452; 548/526; 548/953; 546/205

(58) Field of Classification Search
None
See application file for complete search history.

(56) References Cited

U.S. PATENT DOCUMENTS

| | | | |
|---|---|---|---|
| 2,887,484 A | 5/1959 | Funke | |
| 2,906,757 A | 9/1959 | Mills | |
| 3,058,980 A | 10/1962 | Berg | |
| 3,851,062 A | 11/1974 | Klohs et al. | |
| 4,056,540 A | 11/1977 | Buchanan et al. | |
| 5,126,366 A | 6/1992 | Stack et al. | |
| 5,166,367 A | 11/1992 | Stack et al. | |
| 5,189,171 A | 2/1993 | Stack et al. | |
| 5,235,055 A | 8/1993 | Stack et al. | |
| 5,245,051 A | 9/1993 | Stack et al. | |
| 5,318,988 A | 6/1994 | Schohe-Loop et al. | |
| 5,663,194 A | 9/1997 | Mewshaw | |
| 5,750,724 A | 5/1998 | Kang et al. | |
| 6,903,120 B2 | 6/2005 | Sonesson et al. | |
| 6,924,374 B2 | 8/2005 | Sonesson et al. | |
| 2004/0039023 A1 | 2/2004 | Birch et al. | |
| 2005/0250943 A1 | 11/2005 | Berger et al. | |
| 2005/0282887 A1 | 12/2005 | McComsey et al. | |
| 2006/0041008 A1 | 2/2006 | McComsey et al. | |
| 2006/0069094 A1 | 3/2006 | Bonhaus et al. | |
| 2006/0241172 A1 | 10/2006 | Zhou et al. | |
| 2007/0149542 A1 | 6/2007 | Sonesson et al. | |
| 2007/0155822 A1 | 7/2007 | Smith-Swintosky et al. | |
| 2007/0155823 A1 | 7/2007 | Smith-Swintosky et al. | |
| 2007/0155825 A1 | 7/2007 | Smith-Swintosky et al. | |
| 2007/0155826 A1 | 7/2007 | Smith-Swintosky et al. | |
| 2007/0155827 A1 | 7/2007 | Smith-Swintosky et al. | |
| 2007/0208166 A1 | 9/2007 | Baly et al. | |
| 2007/0244179 A1 | 10/2007 | Greenfield et al. | |
| 2007/0255065 A1 | 11/2007 | Yu et al. | |
| 2007/0293440 A1 | 12/2007 | Smith-Swintosky et al. | |
| 2008/0027131 A1 | 1/2008 | Smith-Swintosky et al. | |
| 2008/0234321 A1 | 9/2008 | Sonesson | |
| 2009/0209634 A1 | 8/2009 | Smith-Swintosky | |
| 2010/0216836 A1 | 8/2010 | Din Belle et al. | |
| 2011/0105461 A1 | 5/2011 | Sonesson et al. | |
| 2011/0105462 A1 | 5/2011 | Sonesson et al. | |

FOREIGN PATENT DOCUMENTS

| WO | WO 96/38435 A1 | 12/1996 |
|---|---|---|
| WO | WO 97/17343 A1 | 5/1997 |
| WO | WO 00/58301 A1 | 10/2000 |
| WO | WO 01/72741 A2 | 10/2001 |
| WO | WO 03/029238 A1 | 4/2003 |
| WO | WO 2005/105776 A1 | 11/2005 |
| WO | WO 2006/007435 A1 | 1/2006 |
| WO | WO 2006/116158 A1 | 11/2006 |
| WO | WO 2009/013390 A1 | 1/2009 |
| WO | WO 2009/133107 A1 | 11/2009 |
| WO | WO 2009/133109 A1 | 11/2009 |

OTHER PUBLICATIONS

Depoortere, et al., Neuropsychopharmacology, 28:1889 (2003).*
Hörig et al., J. Translational Med. 2:44 (2004).*
Avner et al., "1,4-Benzodioxanes as Reversible and Irreversible Antagonists at Adrenergic Receptors", Journal of Medicinal Chemistry, vol. 17, No. 2, pp. 197-200, (1974).
Database Beilstein, Accession No. 278932, Acta Polytechnica Scandinavica, Chemistry Metallurgy Series, 6, pp. 1-48, (1960). XP002541489.
Funke et al., Synthesis of 7-substituted-2-aminomethyl-1,4-bensodioxans, Gazzetta Chimica Italiana, vol. 91, pp. 1268-1281, (1961). XP002541487.

(Continued)

Primary Examiner — Michael Barker
(74) Attorney, Agent, or Firm — Birch, Stewart, Kolasch & Birch, LLP

(57) ABSTRACT

The present invention relates to novel 1-(4H-1,3-benzodioxin-2-yl)methanamine derivatives, useful as modulators of dopamine neurotransmission, and more specifically asdopaminergic stabilizers. In other aspects the invention relates to the use of these compounds in a method for therapy and to pharmaceutical compositions comprising the compounds of the invention.

12 Claims, No Drawings

OTHER PUBLICATIONS

Grafe et al., "Substances synthesized on purpose for antiviral chemotherapy.1. Benzodioxzanes and 2-amino-4-phenylthiazoles", Arzneimittel-Forschung, vol. 24, No. 2, pp. 153-157, (1974).

Itazaki et al., "Synthesis of 2, 3-dihydro-1, 4-benzodioxin derivatives. I. 2-substituted-5(and 6)-sulfannoyl-2,3-dihydro-1,4-benzodioxins", Chemical & Pharmaceutical Bulletin, vol. 36, No. 9, pp. 3387-3403, (1988).

Marini-Bettolo et al., "Benzodioxans. VII. 7-Substituted-2-aminomethyl-1,4-benzodioxans", Croatica Chemica Acta, vol. 29, pp. 363-367, (1957). XP002541486.

Marini-Bettolo et al., "Benzodioxans. VII. Amino alcohols of the 1, 4-benzodioxan series", Gazzetta Chimica Italiana, vol. 87, pp. 1303-1305, (1957). XP002541488.

Marini-Bettolo et al., DataBase Caplus, Accession No. 1958:92883, Chemical Abstracts Service, Columbus, al., "Benzodioxane series. VIII. Amino alcohols of the 1,4-benzodioxan series", (1957). XP002541490.

Mewshaw et al., "New Generation Dopaminergic Agents. Discovery of a Novel Scaffold which Embraces the D2 Agonist Pharmacophore. Structure-Activity Relationships of a Series of 2-(Aminomethyl)chromans", Journal of Medicinal Chemistry, vol. 40, No. 26, pp. 4235-4256, (1997). XP-002155829.

Timmermans et al., "Identical Antagonist Selectivity of Central and Peripheral Alpha1-Adrenoceptors", Molecular Pharmacology, vol. 20, No. 2, pp. 295-301, (1981).

Timmermans et al., Selectivity of Benzodioxane a-Adrenoceptor Determined by Binding Affinity, Pharmacology, vol. 26, No. 5, pp. 258-269, (1983).

* cited by examiner

MODULATORS OF DOPAMINE NEUROTRANSMISSION

This application is a National Phase of PCT/EP2009/055140 filed on Apr. 28, 2009, which claims priority under 35 U.S.C. 119(e) to U.S. Provisional Application No. 61/049,057 filed Apr. 30, 2008 and under 35 U.S.C. 119(a) to Patent Application No. 2008 00600 filed in Denmark, on Apr. 29, 2008, all of which are hereby expressly incorporated by reference into the present application.

FIELD OF THE INVENTION

The present invention relates to novel 1-(4H-1,3-benzodioxin-2-yl)methanamine derivatives, useful as modulators of dopamine neurotransmission, and more specifically as dopaminergic stabilizers.

In other aspects the invention relates to the use of these compounds in a method for therapy and to pharmaceutical compositions comprising the compounds of the invention.

BACKGROUND OF THE INVENTION

Dopamine is a neurotransmitter in the brain. Since this discovery, made in the 1950's, the function of dopamine in the brain has been intensely explored. To date, it is well established that dopamine is essential in several aspects of brain function including motor, cognitive, sensory, emotional and autonomous functions (e.g. regulation of appetite, body temperature, sleep). Thus, modulation of dopaminergic function may be beneficial in the treatment of a wide range of disorders affecting brain functions. In fact, drugs that act, directly or indirectly at central dopamine receptors are commonly used in the treatment of neurological and psychiatric disorders, e.g. Parkinson's disease and schizophrenia. However, currently available dopaminergic pharmaceuticals can have severe side effects. One class of compounds acting through the dopamine systems of the brain are dopaminergic stabilizers, which have shown to be useful in the treatment of both neurologic and psychiatric disorders The typical pharmacological effects which are characteristic for dopaminergic stabilizers can be summarised as: 1) Increased turnover of dopamine in the terminal areas of the ascending dopaminergic projections of the mammalian brain; 2) No or only weak behavioural effects in otherwise untreated rats; and 3) Inhibition of behavioural effects induced by psychostimulants or psychotomimetic compounds in the rat. In the present invention this is referred to as a dopaminergic stabilizer profile.

U.S. Pat. No. 4,056,540 describes certain 4-phenyl-1,3-benzodioxane derivatives useful as anticonvulsive and antiarrhytmic agents. However, the 1-(4H-1,3-benzodioxin-2-yl)methanamine derivatives of the present invention are not suggested.

SUMMARY OF THE INVENTION

The object of the present invention is to provide novel pharmaceutically active compounds, especially useful in treatment of disorders in the central nervous system. A further object is the provision of compounds for modulation of dopaminergic systems in the mammalian brain, including human brain. A still further object is the provision of novel compounds with a dopaminergic stabilizer profile. A further object is to provide compounds with therapeutic effects after oral administration. A still further object is the provision of compounds with more optimal pharmacodynamic properties such as e.g. kinetic behaviour, bioavailability, solubility and efficacy. A further object is to provide compounds being superior to presently known dopaminergic compounds in the treatment of several disorders related to dysfunctions of the CNS, in terms of efficacy or side effects.

The present invention concerns the unexpected discovery of the pharmacological effects of compounds of Formula 1 on the dopaminergic system in the brain. By pharmacological testing in vivo in the rat it is demonstrated that the compounds of the present invention have effects on biochemical indices in the brain with the characteristic features of dopamine antagonists.

In its first aspect, the invention provides a compound of Formula 1

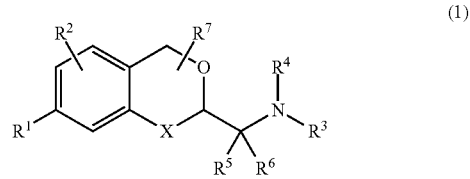

any of its stereoisomers or any mixture of its stereoisomers, or an N-oxide thereof, or a pharmaceutically acceptable salt thereof; wherein $R^1$, $R^2$, $R^3$, $R^4$, $R^5$, $R^6$, $R^7$ and X are as defined below.

In its second aspect, the invention provides a pharmaceutical composition, comprising a therapeutically effective amount of a compound of the invention, any of its stereoisomers or any mixture of its stereoisomers, or an N-oxide thereof, or a pharmaceutically acceptable salt thereof, together with at least one pharmaceutically acceptable carrier, excipient or diluent.

In a further aspect, the invention provides the use of a compound of the invention, any of its stereoisomers or any mixture of its stereoisomers or an N-oxide thereof, or a pharmaceutically acceptable salt thereof, for the manufacture of a pharmaceutical composition for the treatment, prevention or alleviation of a disease or a disorder or a condition of a mammal, including a human, which disease, disorder or condition is responsive to responsive to modulation of dopaminergic function in the central nervous system.

In a still further aspect, the invention relates to a method for treatment, prevention or alleviation of a disease or a disorder or a condition of a living animal body, including a human, which disorder, disease or condition is responsive to modulation of dopaminergic function in the central nervous system, which method comprises the step of administering to such a living animal body in need thereof a therapeutically effective amount of a compound of the invention, any of its stereoisomers or any mixture of its stereoisomers, or an N-oxide thereof, or a pharmaceutically acceptable salt thereof.

Other aspects of the invention will be apparent to the person skilled in the art from the following detailed description and examples.

DETAILED DESCRIPTION OF THE INVENTION

1-(4H-1,3-benzodioxin-2-yl)methanamine Derivatives

In its first aspect the present invention provides compounds of Formula 1:

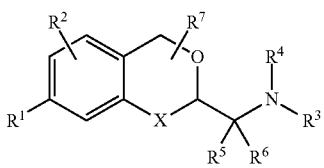
(1)

any of its stereoisomers or any mixture of its stereoisomers, or an N-oxide thereof, or a pharmaceutically acceptable salt thereof, wherein X is O, S, NH or $CH_2$;

$R^1$ is selected from the group consisting of $OSO_2CF_3$, $OSO_2CH_3$, $NHSO_2CH_3$, $NHSO_2CF_3$, $SOR^8$, $SO_2R^8$, $SO_2NH_2$, $SO_2NHCH_3$, $SO_2N(CH_3)_2$, $COR^8$, $CSR^8$, CN, $OCF_3$, $SCF_3$, $OCHF_2$, $SCHF_2$, $CF_3$, F, Cl, Br, I, $NO_2$, $SF_5$, SCN, OCN, $OCOCF_3$, $SCOCF_3$, $OCOCH_3$, $SCOCH_3$ and $CH(OH)CF_3$;

$R^2$ is selected from the group consisting of H, CN, F, Cl, Br, I and $CH_3$;

$R^3$ is selected from the group consisting of $C_1$-$C_5$ alkyl, allyl, $CH_2CH_2OCH_3$, $CH_2CH_2CH_2F$, $CH_2CH_2CHF_2$, $CH_2CH_2F$, 3,3,3-trifluoropropyl, 4,4,4-trifluorobutyl, $CH_2CH_2OH$, $CH_2CH_2CH_2OH$, $CH_2CH(OH)CH_3$, $CH_2CH_2COCH_3$, $C_3$-$C_6$ cycloalkyl,

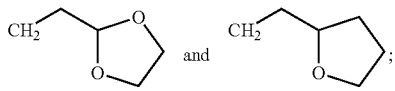

and $R^4$ is selected from the group consisting of H, $C_1$-$C_5$ alkyl, allyl, $CH_2CH_2OCH_3$, $CH_2CH_2CH_2F$, $CH_2CH_2CHF_2$, $CH_2CH_2F$, 3,3,3-trifluoropropyl, 4,4,4-trifluorobutyl, $CH_2CH_2OH$, $CH_2CH_2CH_2OH$, $CH_2CH(OH)CH_3$, $CH_2CH_2COCH_3$,

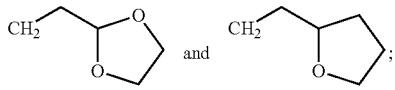

or $R^3$ and $R^4$ together with the nitrogen atom to which they are attached form a four- to six-membered heterocyclic ring, which heterocyclic ring may optionally comprise as a ring member, one oxygen atom, and/or one additional nitrogen atom; and which heterocyclic ring may optionally be substituted with $C_1$-$C_5$ alkyl; and $R^5$, $R^6$ and $R^7$ are selected from the group consisting of H and $CH_3$;

$R^8$ is selected from the group consisting of $C_1$-$C_3$ alkyl, $CF_3$, $CHF_2$, $CH_2F$ and CN.

In a preferred embodiment the compound of the invention is a compound of Formula 1, any of its stereoisomers or any mixture of its stereoisomers, or an N-oxide thereof, or a pharmaceutically acceptable salt thereof, wherein X is O, S, NH or $CH_2$.

In a more preferred embodiment X is O.

In another more preferred embodiment X is S.

In a third more preferred embodiment X is NH.

In a fourth more preferred embodiment X is $CH_2$.

In another preferred embodiment the compound of the invention is a compound of Formula 1, any of its stereoisomers or any mixture of its stereoisomers, or an N-oxide thereof, or a pharmaceutically acceptable salt thereof, wherein $R^1$ is selected from the group consisting of $OSO_2CF_3$, $OSO_2CH_3$, $NHSO_2CH_3$, $NHSO_2CF_3$, $SOR^8$, $SO_2R^8$, $SO_2NH_2$, $SO_2NHCH_3$, $SO_2N(CH_3)_2$, $COR^8$, $CSR^8$, CN, $OCF_3$, $SCF_3$, $OCHF_2$, $SCHF_2$, $CF_3$, F, Cl, Br, I, $NO_2$, $SF_5$, SCN, OCN, $OCOCF_3$, $SCOCF_3$, $OCOCH_3$, $SCOCH_3$ and $CH(OH)CF_3$; and $R^8$ is selected from the group consisting of $C_1$-$C_3$ alkyl, $CF_3$, $CHF_2$, $CH_2F$ and CN.

In a more preferred embodiment $R^1$ is $OSO_2CF_3$.

In another more preferred embodiment $R^1$ is $OSO_2CH_3$.

In a third more preferred embodiment $R^1$ is $NHSO_2CH_3$.

In a fourth more preferred embodiment $R^1$ is $NHSO_2CF_3$.

In a fifth more preferred embodiment $R^1$ is $SOR^8$; and $R^8$ is selected from the group consisting of $C_1$-$C_3$ alkyl, $CF_3$, $CHF_2$, $CH_2F$ and CN.

In a sixth more preferred embodiment $R^1$ is $SO_2R^8$; and $R^8$ is selected from the group consisting of $C_1$-$C_3$ alkyl, $CF_3$, $CHF_2$, $CH_2F$ and CN.

In a seventh more preferred embodiment $R^1$ is $SO_2R^8$; and $R^8$ is $C_1$-$C_3$ alkyl or $CF_3$.

In an eight more preferred embodiment $R^1$ is $SO_2NH_2$.

In a ninth more preferred embodiment $R^1$ is $SO_2NHCH_3$.

In a tenth more preferred embodiment $R^1$ is $SO_2N(CH_3)_2$.

In an eleventh more preferred embodiment $R^1$ is $COR^8$; and $R^8$ is selected from the group consisting of $C_1$-$C_3$ alkyl, $CF_3$, $CHF_2$, $CH_2F$ and CN.

In a twelfth more preferred embodiment $R^1$ is $CSR^8$; and $R^8$ is selected from the group consisting of $C_1$-$C_3$ alkyl, $CF_3$, $CHF_2$, $CH_2F$ and CN.

In a thirteenth more preferred embodiment $R^1$ is CN.

In a fourteenth more preferred embodiment $R^1$ is $OCF_3$.

In a fifteenth more preferred embodiment $R^1$ is $SCF_3$.

In a sixteenth more preferred embodiment $R^1$ is $OCHF_2$.

In a seventeenth more preferred embodiment $R^1$ is $SCHF_2$.

In an eighteenth more preferred embodiment $R^1$ is $CF_3$.

In a nineteenth more preferred embodiment $R^1$ is F.

In a twentieth more preferred embodiment $R^1$ is Cl.

In a twenty first more preferred embodiment $R^1$ is Br.

In a twenty second more preferred embodiment $R^1$ is I.

In a twenty third more preferred embodiment $R^1$ is $NO_2$.

In a twenty fourth more preferred embodiment $R^1$ is $SF_5$.

In a twenty fifth more preferred embodiment $R^1$ is SCN.

In a twenty sixth more preferred embodiment $R^1$ is OCN, $OCOCF_3$, $SCOCF_3$, $OCOCH_3$, $SCOCH_3$ and $CH(OH)CF_3$.

In a twenty seventh more preferred embodiment $R^1$ is $OCOCF_3$.

In a twenty eight more preferred embodiment $R^1$ is $SCOCF_3$.

In a twenty ninth more preferred embodiment $R^1$ is $OCOCH_3$.

In a thirtieth more preferred embodiment $R^1$ is $SCOCH_3$.

In a thirty first more preferred embodiment $R^1$ is $CH(OH)CF_3$.

In a thirty second more preferred embodiment $R^1$ is selected from the group consisting $SO_2CH_3$, $SO_2CF_3$, $CF_3$ and Br.

In a third preferred embodiment the compound of the invention is a compound of Formula 1, any of its stereoisomers or any mixture of its stereoisomers, or an N-oxide thereof, or a pharmaceutically acceptable salt thereof, wherein $R^2$ is selected from the group consisting of H, ON, F, Cl, Br, I and $CH_3$.

In a more preferred embodiment $R^2$ is H.

In another more preferred embodiment $R^2$ is CN.

In a third more preferred embodiment $R^2$ is F.
In a fourth more preferred embodiment $R^2$ is Cl.
In a fifth more preferred embodiment $R^2$ is Br.
In a sixth more preferred embodiment $R^2$ is I.
In a seventh more preferred embodiment $R^2$ is $CH_3$.
In an eight more preferred embodiment $R^2$ is selected from the group consisting of H, F and Cl.
In a ninth more preferred embodiment $R^2$ is H or F.

In a fourth preferred embodiment the compound of the invention is a compound of Formula 1, any of its stereoisomers or any mixture of its stereoisomers, or an N-oxide thereof, or a pharmaceutically acceptable salt thereof, wherein $R^3$ is selected from the group consisting of $C_1$-$C_5$ alkyl, allyl, $CH_2CH_2OCH_3$, $CH_2CH_2CH_2F$, $CH_2CH_2CHF_2$, $CH_2CH_2F$, 3,3,3-trifluoropropyl, 4,4,4-trifluorobutyl, $CH_2CH_2OH$, $CH_2CH_2CH_2OH$, $CH_2CH(OH)CH_3$, $CH_2CH_2COCH_3$, $C_3$-$C_6$ cycloalkyl,

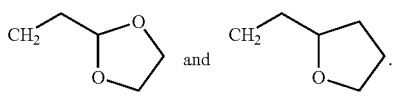

In a more preferred embodiment $R^3$ is $C_1$-$C_5$ alkyl.
In another more preferred embodiment $R^3$ is allyl.
In a third more preferred embodiment $R^3$ is $CH_2CH_2OCH_3$.
In a fourth more preferred embodiment $R^3$ is $CH_2CH_2CH_2F$.
In a fifth more preferred embodiment $R^3$ is $CH_2CH_2CHF_2$.
In a sixth more preferred embodiment $R^3$ is $CH_2CH_2F$.
In a seventh more preferred embodiment $R^3$ is 3,3,3-trifluoropropyl.
In an eight more preferred embodiment $R^3$ is 4,4,4-trifluorobutyl.
In a ninth more preferred embodiment $R^3$ is $CH_2CH_2OH$.
In a tenth more preferred embodiment $R^3$ is $CH_2CH_2CH_2OH$.
In an eleventh more preferred embodiment $R^3$ is $CH_2CH(OH)CH_3$.
In a twelfth more preferred embodiment $R^3$ is $CH_2CH_2COCH_3$.
In a thirteenth more preferred embodiment $R^3$ is $C_3$-$C_6$ cycloalkyl.
In a fourteenth more preferred embodiment $R^3$ is

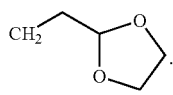

In a fifteenth more preferred embodiment $R^3$ is

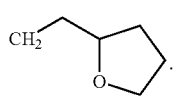

In a sixteenth more preferred embodiment $R^3$ is selected from the group consisting of $C_1$-$C_5$ alkyl, allyl, $CH_2CH_2OCH_3$ and $CH_2CH_2OH$.

In a fifth preferred embodiment the compound of the invention is a compound of Formula 1, any of its stereoisomers or any mixture of its stereoisomers, or an N-oxide thereof, or a pharmaceutically acceptable salt thereof, wherein $R^4$ is selected from the group consisting of H, $C_1$-$C_5$ alkyl, allyl, $CH_2CH_2OCH_3$, $CH_2CH_2CH_2F$, $CH_2CH_2CHF_2$, $CH_2CH_2F$, 3,3,3-trifluoropropyl, 4,4,4-trifluorobutyl, $CH_2CH_2OH$, $CH_2CH_2CH_2OH$, $CH_2CH(OH)CH_3$, $CH_2CH_2COCH_3$,

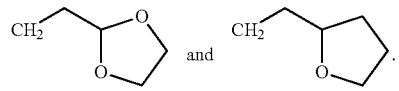

In a more preferred embodiment $R^4$ is H.
In another more preferred embodiment $R^4$ is $C_1$-$C_5$ alkyl.
In a third more preferred embodiment $R^4$ is allyl.
In a fourth more preferred embodiment $R^4$ is $CH_2CH_2OCH_3$.
In a fifth more preferred embodiment $R^4$ is $CH_2CH_2CH_2F$
In a sixth more preferred embodiment $R^4$ is $CH_2CH_2CHF_2$.
In a seventh more preferred embodiment $R^4$ is $CH_2CH_2F$.
In an eight more preferred embodiment $R^4$ is 3,3,3-trifluoropropyl.
In a ninth more preferred embodiment $R^4$ is 4,4,4-trifluorobutyl.
In a tenth more preferred embodiment $R^4$ is $CH_2CH_2OH$.
In an eleventh more preferred embodiment $R^4$ is $CH_2CH_2CH_2OH$.
In a twelfth more preferred embodiment $R^4$ is $CH_2CH(OH)CH_3$.
In a thirteenth more preferred embodiment $R^4$ is $CH_2CH_2COCH_3$.
In a fourteenth more preferred embodiment $R^4$ is

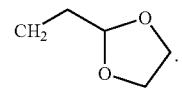

In a fifteenth more preferred embodiment $R^4$ is

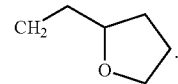

In a sixteenth more preferred embodiment $R^4$ is selected from the group consisting of H and $C_1$-$C_5$ alkyl.

In a sixth preferred embodiment the compound of the invention is a compound of Formula 1, any of its stereoisomers or any mixture of its stereoisomers, or an N-oxide thereof, or a pharmaceutically acceptable salt thereof, wherein $R^3$ and $R^4$ together with the nitrogen atom to which they are attached form a four- to six-membered heterocyclic ring, which heterocyclic ring may optionally comprise as a ring member, one oxygen atom, and/or one additional nitrogen atom; and which heterocyclic ring may optionally be substituted with $C_1$-$C_5$ alkyl.

In a more preferred embodiment $R^3$ and $R^4$ together with the nitrogen atom to which they are attached form a four- to six-membered heterocyclic ring, which heterocyclic ring may optionally comprise as a ring member, one oxygen atom; and which heterocyclic ring may optionally be substituted with $C_1$-$C_5$ alkyl.

In another more preferred embodiment $R^3$ and $R^4$ together with the nitrogen atom to which they are attached form a four- to six-membered heterocyclic ring.

In a third more preferred embodiment $R^3$ and $R^4$ together with the nitrogen atom to which they are attached form a four-membered heterocyclic ring, which heterocyclic ring may optionally be substituted with $C_1$-$C_5$ alkyl.

In a fourth more preferred embodiment $R^3$ and $R^4$ together with the nitrogen atom to which they are attached form a five-membered heterocyclic ring, which heterocyclic ring may optionally be substituted with $C_1$-$C_5$ alkyl.

In a fifth more preferred embodiment $R^3$ and $R^4$ together with the nitrogen atom to which they are attached form a six-membered heterocyclic ring, which heterocyclic ring may optionally comprise as a ring member, one oxygen atom, and which heterocyclic ring may optionally be substituted with $C_1$-$C_5$ alkyl.

In a sixth more preferred embodiment $R^3$ and $R^4$ together the nitrogen atom to which they are attached form acetidine, pyrrolidine, piperidine or morpholine.

In a seventh more preferred embodiment $R^3$ and $R^4$ together the nitrogen atom to which they are attached form an acetidine group.

In an eight more preferred embodiment $R^3$ and $R^4$ together the nitrogen atom to which they are attached form a pyrrolidine group.

In a ninth more preferred embodiment $R^3$ and $R^4$ together the nitrogen atom to which they are attached form a piperidine group.

In a tenth more preferred embodiment $R^3$ and $R^4$ together the nitrogen atom to which they are attached form a morpholine group.

In a seventh preferred embodiment the compound of the invention is a compound of Formula 1, any of its stereoisomers or any mixture of its stereoisomers, or an N-oxide thereof, or a pharmaceutically acceptable salt thereof, wherein $R^5$, $R^6$ and $R^7$ are selected from the group consisting of H and $CH_3$.

In a more preferred embodiment each of $R^5$, $R^6$ and $R^7$ is H.

In a further preferred embodiment the compound of the invention is
N-{[7-(TRIFLUOROMETHYL)-4H-1,3-BENZODIOXIN-2-YL]METHYL}PROPAN-1-AMIN;
1-{[7-(METHYLSULFONYL)-4H-1,3-BENZODIOXIN-2-YL]METHYL}PYRROLIDINE;
N-{[7-(METHYLSULFONYL)-4H-1,3-BENZODIOXIN-2-YL]METHYL}PROPAN-1-AMINE;
(−)-N-{[7-(METHYLSULFONYL)-4H-1,3-BENZODIOXIN-2-YL]METHYL}PROPAN-1-AMINE;
(+)-N-{[7-(METHYLSULFONYL)-4H-1,3-BENZODIOXIN-2-YL]METHYL}PROPAN-1-AMINE;
N-{[7-(METHYLSULFONYL)-4H-1,3-BENZODIOXIN-2-YL]METHYL}PROPAN-2-AMINE;
1-({7-[(TRIFLUOROMETHYL)SULFONYL]-4H-1,3-BENZODIOXIN-2-YL}METHYL)PYRROLIDINE;
N-({7-[(TRIFLUOROMETHYL)SULFONYL]-4H-1,3-BENZODIOXIN-2-YL}METHYL)PROPAN-1-AMINE;
N-{[7-(METHYLSULFONYL)-4H-1,3-BENZODIOXIN-2-YL]METHYL}ETHANAMINE;
(−)-N-{[7-(METHYLSULFONYL)-4H-1,3-BENZODIOXIN-2-YL]METHYL}ETHANAMINE;
(+)-N-{[7-(METHYLSULFONYL)-4H-1,3-BENZODIOXIN-2-YL]METHYL}ETHANAMINE;
N-METHYL-1-[7-(METHYLSULFONYL)-4H-1,3-BENZODIOXIN-2-YL]METHANAMINE;
(−)-N-METHYL-1-[7-(METHYLSULFONYL)-4H-1,3-BENZODIOXIN-2-YL]METHANAMINE;
(+)-N-METHYL-1-[7-(METHYLSULFONYL)-4H-1,3-BENZODIOXIN-2-YL]METANAMINE;
N-({7-[(TRIFLUOROMETHYL)SULFONYL]-4H-1,3-BENZODIOXIN-2-YL}METHYL)ETHANAMINE;
N-[(7-BROMO-5-FLUORO-4H-1,3-BENZODIOXIN-2-YL)METHYL]PROPAN-1-AMINE;
N-{[5-FLUORO-7-(METHYLSULFONYL)-4H-1,3-BENZODIOXIN-2-YL]METHYL}PROPAN-1-AMINE;
1-[5-FLUORO-7-(METHYLSULFONYL)-4H-1,3-BENZODIOXIN-2-YL]-N-METHYLMETHANAMINE;
N-[(7-BROMO-6-FLUORO-4H-1,3-BENZODIOXIN-2-YL)METHYL]PROPAN-1-AMINE;
N-{[6-FLUORO-7-(METHYLSULFONYL)-4H-1,3-BENZODIOXIN-2-YL]METHYL}PROPAN-1-AMINE;
1-{[7-(METHYLSULFONYL)-4H-1,3-BENZODIOXIN-2-YL]METHYL}PIPERIDINE;
N-{[7-(METHYLSULFONYL)-4H-1,3-BENZODIOXIN-2-YL]METHYL}BUTAN-1-AMINE;
2-({[7-(METHYLSULFONYL)-4H-1,3-BENZODIOXIN-2-YL]METHYL}AMINO)ETHANOL;
N-{[7-(METHYLSULFONYL)-4H-1,3-BENZODIOXIN-2-YL]METHYL}-N,N-PROPYLPROPAN-1-AMINE;
N-ETHYL-N-{[7-(METHYLSULFONYL)-4H-1,3-BENZODIOXIN-2-YL]METHYL}-N-PROPAN-1-AMINE;
N-{[7-(METHYLSULFONYL)-4H-1,3-BENZODIOXIN-2-YL]METHYL}PROP-2-EN-1-AMINE;
N,N-DIMETHYL-1-[7-(METHYLSULFONYL)-4H-1,3-BENZODIOXIN-2-YL]METHANAMINE;
N-METHYL-N-{[7-(METHYLSULFONYL)-4H-1,3-BENZODIOXIN-2-YL]METHYL}PROPAN-1-AMINE;
1-{[7-(METHYLSULFONYL)-4H-1,3-BENZODIOXIN-2-YL]METHYL}AZETIDINE;
4-{[7-(METHYLSULFONYL)-4H-1,3-BENZODIOXIN-2-YL]METHYL}MORPHOLINE; 2-METHOXY-N-{[7-(METHYLSULFONYL)-4H-1,3-BENZODIOXIN-2-YL]METHYL}ETHANAMINE;
N-ETHYL-N-{[7-(METHYLSULFONYL)-4H-1,3-BENZODIOXIN-2-YL]METHYL}ETHANAMINE;
N-METHYL-N-{[7-(METHYLSULFONYL)-4H-1,3-BENZODIOXIN-2-YL]METHYL}ETHANAMINE;
N-{[5-FLUORO-7-(METHYLSULFONYL)-4H-1,3-BENZODIOXIN-2-YL]METHYL}ETHANAMINE;
1-{[5-FLUORO-7-(METHYLSULFONYL)-4H-1,3-BENZODIOXIN-2-YL]METHYL}PIPERIDINE;
N-{[5-FLUORO-7-(METHYLSULFONYL)-4H-1,3-BENZODIOXIN-2-YL]METHYL}-2-METHYLPROPAN-1-AMINE;
N-{[5-FLUORO-7-(METHYLSULFONYL)-4H-1,3-BENZODIOXIN-2-YL]METHYL}BUTAN-1-AMINE;
1-{[5-FLUORO-7-(METHYLSULFONYL)-4H-1,3-BENZODIOXIN-2-YL]METHYL}PYRROLIDINE;
N-{[5-FLUORO-7-(METHYLSULFONYL)-4H-1,3-BENZODIOXIN-2-YL]METHYL}PROP-2-EN-1-AMINE;
N-{[5-FLUORO-7-(METHYLSULFONYL)-4H-1,3-BENZODIOXIN-2-YL]METHYL}-N-PROPYLPROPAN-1-AMINE;
1-[5-FLUORO-7-(METHYLSULFONYL)-4H-1,3-BENZODIOXIN-2-YL]-N,N-DIMETHYLMETHANAMINE;
N-ETHYL-N-{[5-FLUORO-7-(METHYLSULFONYL)-4H-1,3-BENZODIOXIN-2-YL]METHYL}ETHANAMINE;
N-{[5-FLUORO-7-(METHYLSULFONYL)-4H-1,3-BENZODIOXIN-2-YL]METHYL}PROPAN-2-AMINE;
N-{[5-FLUORO-7-(METHYLSULFONYL)-4H-1,3-BENZODIOXIN-2-YL]METHYL}-N-METHYLPROPAN-1-AMINE;

N-ETHYL-N-{[5-FLUORO-7-(METHYLSULFONYL)-4H-1,3-BENZODIOXIN-2-YL]METHYL}PROPAN-1-AMINE;

N-{[5-FLUORO-7-(METHYLSULFONYL)-4H-1,3-BENZODIOXIN-2-YL]METHYL}-N-METHYLETHANAMINE;

N-{[5-FLUORO-7-(METHYLSULFONYL)-4H-1,3-BENZODIOXIN-2-YL]METHYL}-2-METHOXYETHANAMINE;

1-{[5-FLUORO-7-(METHYLSULFONYL)-4H-1,3-BENZODIOXIN-2-YL]METHYL}AZETIDINE;

N-{[5-FLUORO-7-(METHYLSULFONYL)-4H-1,3-BENZODIOXIN-2-YL]METHYL}-2,2-DIMETHYLPROPAN-1-AMINE; or

3-FLUORO-N-{[5-FLUORO-7-(METHYLSULFONYL)-4H-1,3-BENZODIOXIN-2-YL]METHYL}PROPAN-1-AMINE;

any of its stereoisomers or any mixture of its stereoisomers, or an N-oxide thereof, or a pharmaceutically acceptable salt thereof.

Any combination of two or more of the embodiments as described above is considered within the scope of the present invention.

Definition of Substituents

In the context of this invention $C_1$-$C_5$ alkyl means a straight chain or branched chain of one to five carbon atoms, including but not limited to, methyl, ethyl, n-propyl, i-propyl, n-butyl, i-butyl, s-butyl, t-butyl, n-pentyl, i-pentyl, neo-pentyl.

$C_3$-$C_6$ cycloalkyl designates a cyclic alkyl group containing of from three to six carbon atoms, including cyclopropyl, cyclobutyl and cyclopentyl.

The term "allyl" refers to the group—$CH_2$—CH=$CH_2$.

Four- to six-membered heterocyclic rings comprising at least one nitrogen atom include for example, but not limited to, acetidine, pyrrolidine, piperidine and morpholine.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydro-chloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Examples of pharmaceutically acceptable cationic salts of a chemical compound of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention include compounds modified at one or more reactive or derivatizable groups of the parent compound. Of particular interest are compounds modified at a carboxyl group, a hydroxyl group, or an amino group. Examples of suitable derivatives are esters or amides.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

It will be appreciated by those skilled in the art that the compounds of the present invention may exist in different stereoisomeric forms—including enantiomers, diastereomers or cis-trans-isomers.

The invention includes all such isomers and any mixtures thereof including racemic mixtures.

Racemic forms can be resolved into the optical antipodes by known methods and techniques. One way of separating the enantiomeric compounds (including enantiomeric intermediates) is—in the case the compound being a chiral acid—by use of an optically active amine, and liberating the diastereomeric, resolved salt by treatment with an acid. Another method for resolving racemates into the optical antipodes is based upon chromatography on an optical active matrix. Racemic compounds of the present invention can thus be resolved into their optical antipodes, e.g., by fractional crystallisation of D- or L-(tartrates, mandelates, or camphor-sulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

N-Oxides

In the context of this invention an N-oxide designates an oxide derivative of a tertiary amine, including a nitrogen atom of an aromatic N-heterocyclic compound, a non-aromatic N-heterocyclic compounds, a trialkylamine and a trialkenylamine. For example, the N-oxide of a compound containing a pyridyl may be the 1-oxy-pyridin-2, -3 or -4-yl derivative.

N-oxides of the compounds of the invention may be prepared by oxidation of the corresponding nitrogen base using a conventional oxidizing agent such as hydrogen peroxide in the presence of an acid such as acetic acid at an elevated temperature, or by reaction with a peracid such as peracetic acid in a suitable solvent, e.g. dichloromethane, ethyl acetate or methyl acetate, or in chloroform or dichloromethane with 3-chloroperoxybenzoic acid.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radio-nuclide as a label. Positron emitting radionuclides are all candidates for usage. In the context of this invention the radionuclide is preferably selected from $^2$H (deuterium), $^3$H (tritium), $^{11}$C, $^{13}$C, $^{14}$C, $^{131}$I, $^{125}$I, $^{123}$I and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The chemical compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Persons skilled in the art will appreciate that, in order to obtain compounds of the invention in an alternative—and in some occasions, more convenient manner—the individual process steps mentioned hereinbefore may be performed in a different order, and/or the individual reactions may be performed at different stage in the overall route (i.e. chemical transformations may be performed upon different intermediates to those associated hereinbefore with a particular reaction).

Biological Activity

The typical pharmacological effects which are characteristic for dopaminergic stabilizers are an increased turnover of dopamine in the terminal areas of the ascending dopaminergic projections of the mammalian brain. This can be illustrated by measuring of changes in biochemical indices in the brain with the characteristic features of dopamine antagonists, e.g. producing increases in concentrations of dopamine metabolites such as 3,4-dihydroxyphenyl-acetic acid (DOPAC) in the striatum. The typical increase in DOPAC levels (striatum) possible to achieve is in the range of 350-400% of control.

Representative compounds of the invention are shown in Table 1.

TABLE 1

Estimated $ED_{50}$ values on increase of DOPAC (3,4-dihydroxyphenylacetic acid) in the rat striatum after systemic adminstration of test compound. For methods and statistical calculations see the enclosed tests.

| Examples | $ED_{50}$ DOPAC* μmol/kg |
|---|---|
| Example 1 | 17 (15-20) |
| Example 4 | 27 (23-31) |
| Example 5 | 12 (9.3-14) |
| Example 7 | 48 (38-82) |
| Example 8 | 7.0 (4.5-9.3) |
| Example 16 | 20 (16-25) |
| Example 17 | 8.6 (7.0-10) |
| Example 20 | 11 (7.9-13) |
| Example 21 | 13 (11-16) |

The compounds according to the present invention possess dopamine-modulating properties and both they and their pharmaceutical compositions are useful in treating numerous central nervous system disorders, including both psychiatric and neurological disorders. Particularly, the compounds and their pharmaceutical compositions may be used in the treatment of CNS disorders were the dopaminergic system is dysfunctional due to direct or indirect causes.

The compounds and compositions according to the invention can be used to improve all forms of psychosis, including schizophrenia and schizophreniform and bipolar disorders as well as drug induced psychotic disorders. Iatrogenic psychoses and hallucinoses and non-iatrogenic psychoses and hallucinoses may also be treated.

In a preferred embodiment the disease, disorder or condition contemplatyed according to the invention is a form of psychosis, in particular schizophrenia, a schizophreniform disorder, a bipolar disorder, or a drug induced psychotic disorder.

Mood and anxiety disorders, depression and obsessive-compulsive disease may also be treated with the compounds and compositions according to the invention.

Compounds with modulating effects on dopaminergic systems may also be used to improve motor and cognitive functions and in the treatment of emotional disturbances related to ageing, neurodegenerative (e.g. dementia and age-related cognitive impairment) and developmental disorders (such as Autism spectrum disorders, ADHD, Cerebral Palsy, Gilles de la Tourette's syndrome) as well as after brain injury. Such brain injury may be induced by traumatic, inflammatory, infectious, neoplastic, vascular, hypoxic or metabolic causes or by toxic reactions to exogenous chemicals, wherein the exogenous chemicals are selected from the group consisting of substances of abuse, pharmaceutical compounds and environmental toxins The compounds and pharmaceutical compositions according to the invention may also be used in behavioural disorders usually first diagnosed in infancy, childhood, or adolescence as well as in impulse control disorders.

They can also be used for treating substance abuse disorders as well as disorders characterized by misuse of food. They are further useful for treatment of a condition selected from the group consisting of sleep disorders, sexual disorders, eating disorders, obesitas, and headaches and other pains in conditions characterized by increased muscular tone.

Neurological indications include the use of the compounds and their pharmaceutical compositions to improve mental and motor function in Parkinson's disease, and in related parkinsonian syndromes, dyskinesias (including L-DOPA induced dyskinesias) and dystonias. They may also be used to ameliorate tics and tremor of different origins. Moreover, they may be used to relieve pain in conditions characterized by increased muscle tone.

They can also be used in the treatment of Huntington's disease and other movement disorders as well as movement disorders induced by drugs. Restless legs and related disorders as well as narcolepsy may also be treated with compounds included according to the invention.

The compounds and their pharmaceutical compositions according to the present invention can be used for the treatment of Alzheimer's disease or related dementia disorders.

The effects of compounds of the invention on spontaneous locomotion are shown in Table 2.

TABLE 2

Effects of compounds from the present invention on Locomotor activity in drug-naive rats. The animals were placed in the motility meters immediately after drug administration and locomotor activity was recorded for 60 minutes (counts/60 min ± SEM).

| Example | Control group | 3.7 µmol/kg | 11 µmol/kg | 33 µmol/kg |
|---|---|---|---|---|
| Example 1 | 7041 ± 1291 | 8038 ± 1487 | 7279 ± 968 | 2682 ± 802 |
| Example 4 | 9353 ± 3137 | 9158 ± 2094 | 11153 ± 1257 | 12588 ± 331 |
| Example 5 | 7334 ± 707 | 9173 ± 3160 | 8274 ± 801 | 4854 ± 771 |
| Example 7 | 9103 ± 1319 | 9548 ± 1455 | 7270 ± 278 | 11818 ± 2775 |
| Example 8 | 8687 ± 902 | 11601 ± 583 | 7064 ± 1032 | 2641 ± 757 |
| Example 16 | 8501 ± 1640 | 8637 ± 1217 | 7537 ± 2127 | 7393 ± 1395 |
| Example 17 | 9403 ± 1179 | 10520 ± 1381 | 8330 ± 2194 | 3319 ± 140 |
| Example 20 | 9797 ± 1096 | 8830 ± 1277 | 10181 ± 1385 | 5502 ± 474 |
| Example 21 | 8268 ± 616 | 8285 ± 721 | 6585 ± 707 | 4197 ± 923 |

The effects of compounds of the invention on the increase in activity induced by direct or indirect dopaminergic agonists, i.e. d-amphetamine and congeners are shown in Table 3.

TABLE 3

Effects of compounds in the present invention on reduction of amphetamine-induced hyper-locomotion.

| Example | $ED_{50}$ µmol/kg |
|---|---|
| Example 1 | 3.9 (0.2-12) |
| Example 4 | 27 (19-35) |
| Example 5 | 15 (10-20) |
| Example 7 | 50 (31-73) |
| Example 8 | 4.9 (0.34-13) |
| Example 21 | 14 (5.4-23) |

Pharmaceutical Compositions

In another aspect the invention provides novel pharmaceutical compositions comprising a therapeutically effective amount of the chemical compound of the invention.

The present invention relates to pharmaceutical compositions comprising the compounds of the present invention, and their use in treating CNS disorders. Both organic and inorganic acids can be employed to form non-toxic pharmaceutically acceptable acid addition salts of the compounds according to the invention. Suitable acid addition salts of the compounds of the present invention include those formed with pharmaceutically acceptable salts such as those mentioned above. The pharmaceutical composition comprising a compound according to the invention may also comprise substances used to facilitate the production of the pharmaceutical preparation or the administration of the preparations. Such substances are well known to people skilled in the art and may for instance be pharmaceutically acceptable adjuvants, carriers and preservatives.

In clinical practice, the compounds according to the present invention will normally be administered orally, rectally, nasally or by injection, in the form of pharmaceutical preparations comprising the active ingredient either as a free base or as a pharmaceutically acceptable non-toxic, acid addition salt, such as the hydrochloride, lactate, acetate or sulfamate salt, in association with a pharmaceutically acceptable carrier. The carrier may be a solid, semisolid or liquid preparation. Usually the active substance will constitute between 0.1 and 99% by weight of the preparation, more specifically between 0.5 and 20% by a weight for preparations intended for injection and between 0.2 and 50% by weight for preparations suitable for oral administration.

To produce pharmaceutical preparations containing the compound according to the invention in the form of dosage units for oral application, the selected compound may be mixed with a solid excipient, e.g. lactose, saccharose, sorbitol, mannitol, starches such as potato starch, corn starch or amylopectin, cellulose derivatives, a binder such as gelatine or polyvinyl-pyrrolidine, and a lubricant such as magnesium stearate, calcium stearate, polyethylene glycol, waxes, paraffin, and the like, and then compressed into tablets. If coated tablets are required, the cores (prepared as described above) may be coated with a concentrated sugar solution which may contain e.g. gum arabic, gelatine, talcum, titanium dioxide, and the like. Alternatively, the tablet can be coated with a polymer known to the man skilled in the art, dissolved in a readily volatile organic solvent or mixture of organic solvents. Dyestuffs may be added to these coatings in order to readily distinguish between tablets containing different active substances or different amounts of the active compound.

For the preparation of soft gelatine capsules, the active substance may be admixed with e.g. a vegetable oil or polyethylene glycol. Hard gelatine capsules may contain granules of the active substance using either the mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Examples of tablet and capsule formulations suitable for oral administration are given below:

|  | mg/tablet |
| --- | --- |
| Tablet I | |
| Compound | 100 |
| Lactose Ph.Eur | 182.75 |
| Croscarmellose sodium | 2.0 |
| Maize starch paste (5% w/v paste) | 2.25 |
| Magnesium stearate | 3.0 |
| Tablet II | |
| Compound | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| Tablet III | |
| Compound | 1.0 |
| Lactose Ph.Eur | 93.25 |
| Croscarmellose sodium | 4.0 |
| Maize starch paste (5% w/v paste) | 0.75 |
| Magnesium stearate | 1.0 |
| Capsule | mg/capsule |
| Compound | 10 |
| Lactose Ph.Eur | 488.5 |
| Magnesium | 1.5 |

Dosage units for rectal application can be solutions or suspensions or can be prepared in the form of suppositories comprising the active substance in a mixture with a neutral fatty base, or gelatine rectal capsules comprising the active substance in admixture with vegetable oil or paraffin oil. Liquid preparations for oral application may be in the form of syrups or suspensions, for example solutions containing from about 0.2% to about 20% by weight of the active substance herein described, the balance being sugar and mixture of ethanol, water, glycerol and propylene glycol. Optionally such liquid preparations may contain coloring agents, flavoring agents, saccharine and carboxymethylcellulose as a thickening agent or other excipients known to the man in the art.

Solutions for parenteral applications by injection can be prepared in an aqueous solution of a water-soluble pharmaceutically acceptable salt of the active substance, preferably in a concentration of from 0.5% to about 10% by weight. These solutions may also containing stabilizing agents and/or buffering agents and may conveniently be provided in various dosage unit ampoules. The use and administration to a patient to be treated would be readily apparent to an ordinary skill in the art.

For intranasal administration or administration by inhalation, the compounds of the present invention may be delivered in the form of a solution, dry powder or suspension. Administration may take place via a pump spray container that is squeezed or pumped by the patient or through an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. The compounds of the invention may also be administered via a dry powder inhaler, either as a finely divided powder in combination with a carrier substance (e.g. a saccharide) or as microspheres. The inhaler, pump spray or aerosol spray may be single or multi dose. The dosage may be controlled through a valve that delivers a measured amount of active compound.

The compounds of the invention may also be administered in a controlled release formulation. The compounds are released at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations. The compounds may also be formulated in controlled release formulations in which release of the active compound is targeted. For example, release of the compound may be limited to a specific region of the digestive system through the pH sensitivity of the formulation. Such formulations are well known to persons skilled in the art.

Further details on techniques for formulation and administration may be found in the latest edition of Remington's Pharmaceutical Sciences (Maack Publishing Co., Easton, Pa.).

Depending upon the disorder and patient to be treated and the route of administration, the compositions may be administered at varying doses. The dosing will also depend upon the relation of potency to absorbability and the frequency and route of administration. Such doses may be administered once, twice or three or more times daily. The compounds of this invention can be administered to subjects in doses ranging from 0.01 mg to 500 mg per kg of body weight per day, although variations will necessarily occur depending upon the weight, sex and condition of the subject being treated, the disease state being treated and the particular route of administration chosen. However, a dosage level that is in the range of from 0.1 mg to 10 mg per kg of body weight per day, single or divided dosage is most desirably employed in humans for the treatment of diseases. Alternatively, the dosage level is such that a serum concentration of between 0.1 nM to 10 μM of the compound is obtained.

EXAMPLES

The invention is further illustrated in the examples below and as outlined below in Schemes 1-5, which in no way are intended to limit the scope of the invention.

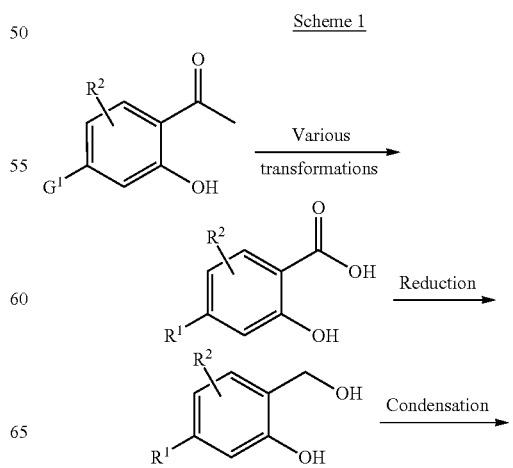

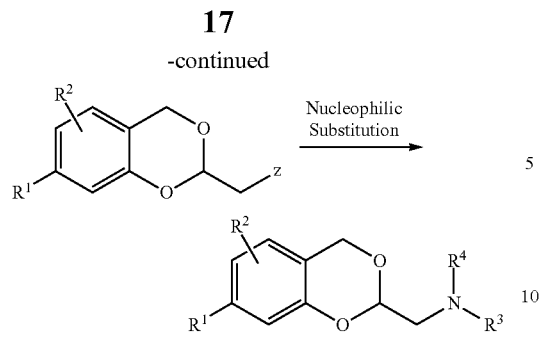
Scheme 2
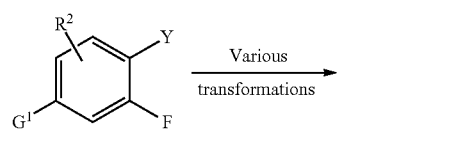
Y = H or Br
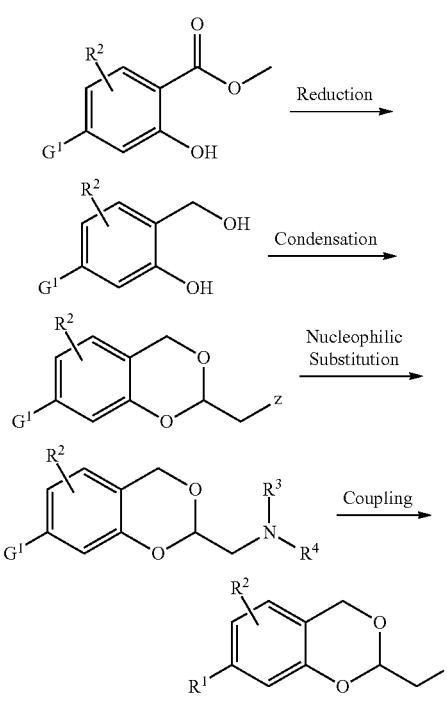
Scheme 3
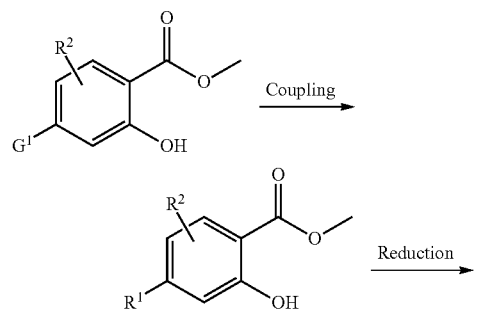
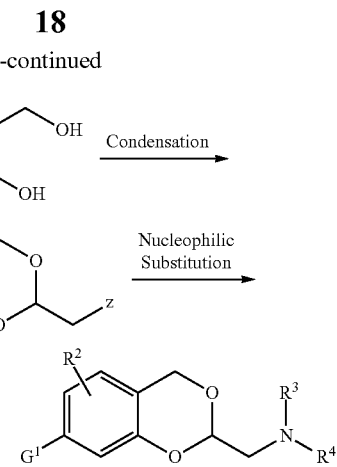
Scheme 4
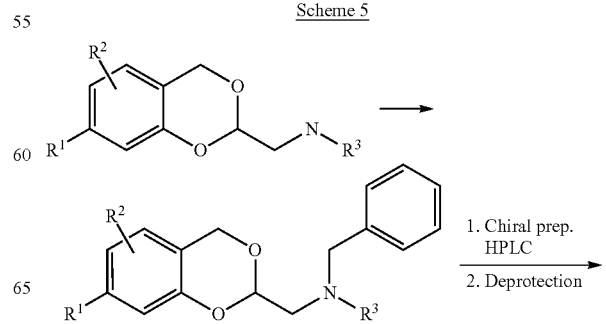
Scheme 5

-continued

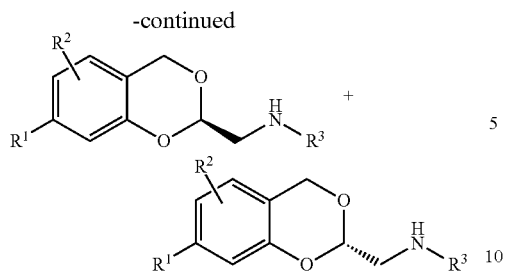

The substituents in Schemes 1-5, are as follows: Z is a leaving group, $G^1$ is $R^1$ or a group that can be transformed into $R^1$, A is alkyl, hydrogen or a protecting group. X, $R^1$, $R^2$ and $R^3$ are as defined above.

Example 1

N-{[7-(TRIFLUOROMETHYL)-4H-1,3-BENZO-DIOXIN-2-YL]METHYL}PROPAN-1-AMIN

A mixture of 2-(chloromethyl)-7-(trifluoromethyl)-4H-1,3-benzodioxine (0.25 g, 1.0 mmol), propan-1-amine (0.81 ml, 10 mmol), potassiumcarbonate (0.17 g, 1.2 mmol), potassiumiodide (2 crystals) in ACN (4 ml) was heated in a microwave oven at 170° C. for 33 min. The reaction mixture was filtered and evaporated under reduced pressure. The crude product was purified by flash column chromatograpy (isooctane/10 EtOAc 1:10) to give the product (0.12 g, 45%). The amine was converted to the hydrochloric acid salt and crystallized from EtOH/DEE. M.p. 203° C. MS m/z (relative intensity, 70 eV) 275 (M+, 3), 175 (18), 146 (8), 127 (14), 72 (bp).

Example 2

1-{[7-(METHYLSULFONYL)-4H-1,3-BENZO-DIOXIN-2-YL]METHYL}PYRROLIDINE

A mixture of 2-(bromomethyl)-7-(methylsulfonyl)-4H-1,3-benzodioxine (0.5 g, 1.63 mmol), pyrrolidine (2.0 ml, 24.0 mmol) and EtOH (4.0 ml) was heated in a micro wave oven at 130° C. for 30 min. The mixture was evaporated to dryness. The residue was chromathographed on a silica column using EtOAc/MeOH (10:1) as eluent, affording the title compound (0.37 g, 76%). The title compound (0.26 g) was converted into the hydrochloric acid salt and crystallized from EtOH/DEE. M.p. 199° C. $^1$H-NMR (400 MHz, MeOH): δ 7.49 (1H, dd, J 18 Hz, J 21.6 Hz), δ 7.40 (1H, d, J 1.6 Hz), δ 7.31 (1H, d, J 8 Hz), 5.29 (1H, t, J 4.4 Hz), δ 5.03 (2H, dd, J 56 Hz, 16 Hz), δ 3.1 (3H, s), 2.92 (2H, m), δ 2.70 (4H, m), δ 1.83 (4H, m).

Example 3

N-{[7-(METHYLSULFONYL)-4H-1,3-BENZO-DIOXIN-2-YL]METHYL}PROPAN-1-AMINE

A mixture of 2-(bromomethyl)-7-(methylsulfonyl)-4H-1,3-benzodioxine (0.50 g, 1.63 mmol), propan-1-amine (2.0 ml, 24.3 mmol), EtOH (3.0 ml) was heated in a micro wave oven at 140° C. for 30 min. The mixture was evaporated to dryness. The residue was chromathographed on a silica column using EtOAc:MeOH (5:1) as eluent, affording the title compound as a light-yellow solid (0.56 g). The product was washed with several portions of ethyl acetate to give a pure white powder as the title compound (0.43 g, 90%). 0.24 g of the title compound was converted into the hydrochloric acid salt and crystallized from EtOH/DEE. M.p. 213° C. MS m/z (rel. intensity, 70 eV) 285 (M+, 1), 123 (10), 77 (15), 72 (bp), 51 (12).

Example 4

(−)-N-{[7-(METHYLSULFONYL)-4H-1,3-BENZODIOXIN-2-YL]METHYL}PROPAN-1-AMINE (−)-N-benzyl-N-{[7-(methylsulfonyl)-4H-1,3-benzodioxin-2-yl]methyl}propan-1-amine (0.25 g, 0.67 mmol), palladium on carbon (10%, 30 mg), concentrated AcOH (0.1 ml) and EtOH (15 ml) was hydrogenated at 40 psi for 1 h. The reaction mixture was filtered through a pad of celite and the filtrate was evaporated to dryness. The crude product was dissolved in EtOAc (100 ml) and basified with $Na_2CO_3$ (10%, 50 ml). The layers were separated and the aqueous layer was extracted with EtOAc (2×75 ml). The combined organic layers were collected, dried ($Na_2SO_4$), filtered and evaporated to dryness (0.32 g). Purification by flash chromatography (EtOAc/MeOH 10:1) afforded the pure title compound (0.13 g, 71%, >95% e.e.). The amine was converted into the hydrochloric acid salt and crystallized from EtOH/MeOH/DEE. M.p. 235° C. $[α]^D_{MeOH}$=−80°. $^1$H-NMR (400 MHz, MeOH): δ 7.49 (1H, dd, J1 8.0 Hz J2 2.0 Hz), δ 7.41 (1H, d, 2.0 Hz), δ 7.30 (1H, d, J 8 Hz), δ 5.25 (1H, t, J 5.2 Hz), δ 5.02 (2H, dd, J1 50 Hz, J2 16 Hz), δ 3.1 (3H, s), δ 2.97 (2H, m), δ 2.65 (2H, t, J 7.2 Hz), δ 1.56 (2H, m), δ 0.95 (3H, t, J 7.6 Hz).

Example 5

(+)-N-{[7-(METHYLSULFONYL)-4H-1,3-BENZODIOXIN-2-YL]METHYL}PROPAN-1-AMINE

Preparation according to Example 4. (+)-N-benzyl-N-{[7-(methylsulfonyl)-4H-1,3-benzodioxin-2-yl]methyl}propan-1-amine (0.21 g, 0.56 mmol), palladium on carbon (10%, 25 mg), concentrated AcOH (0.1 ml) and EtOH (10 ml) was hydrogenated at 40 psi for 1 h 15 min. Purification afforded the title compound (0.14 g, 83%, >95% e.e.) The amine was converted into the hydrochloric acid salt and crystallized from EtOH/MeOH/DEE. M.p. 235° C. $[α]^D_{MeOH}$=+77°. $^1$H-NMR (400 MHz, MeOH): δ 7.50 (1H, dd, J1 8.4 Hz J2 2.0 Hz), δ 7.41 (1H, d, J 1.6 Hz), δ 7.31 (1H, d, J 7.6 Hz), δ 5.25 (1H, t, J 5.2 Hz), δ 5.03 (2H, dd, J1 50 Hz, J2 16 Hz), δ 3.10 (3H, s), δ 2.97 (2H, m), δ 2.65 (2H, t, J 7.2 Hz), δ 1.56 (2H, m), δ 0.95 (3H, t, J 7.6 Hz).

Example 6

N-{[7-(METHYLSULFONYL)-4H-1,3-BENZODIOXIN-2-YL]METHYL}PROPAN-2-AMINE

A mixture of 2-(chloromethyl)-7-(methylsulfonyl)-4H-1,3-benzodioxine (0.1 g, 0.38 mmol), propan-2-amine (1.30 ml, 152 mmol), potassium carbonate (80 mg, 0.57 mmol), some few crystals of sodium iodide in ACN (3 ml) was heated in a micro wave oven at 170° C. for 40 min. After cooling to ambient temperature the volatiles were evaporated in vacuum. The oily residue was chromatographed twice on a silica column with EtOAc/MeOH (7:1) as eluent. Collection of the fractions containing pure product and evaporation of the solvent afforded the title compound (61 mg, 55%). MS m/z (rel. intensity, 70 eV) 285 (M+, 1), 123 (11), 86 (15), 77 (16), 72 (bp).

Example 7

1-({7-[(TRIFLUOROMETHYL)SULFONYL]-4H-1,3-BENZODIOXIN-2-YL}METHYL)PYRROLIDINE

A mixture of 2-(bromomethyl)-7-[(trifluoromethyl)sulfonyl]-4H-1,3-benzodioxine (0.40 g, 1.11 mmol), pyrrolidine (0.47 ml, 5.5 mmol), potassiumcarbonate (0.23 g, 1.7 mmol) and ACN (3.0 ml) was heated in a micro wave oven at 150° C. for 15 min. The mixture was filtered and evaporated to dryness. The residue was purified two times on a silica column using EtOAc/MeOH (4:1) and EtOAc/MeOH (9:1) as eluents. The pure fractions were collected and evaporated to afford the title product (0.19 g, 48%). The amine was converted into the fumaric acid salt and crystallized from EtOH/MeOH/DEE. M.p. 184° C. MS m/z (rel. intensity, 70 eV) 351 (M+, 5), 85 (6), 84 (bp), 76 (5), 55 (4).

Example 8

N-({7-[(TRIFLUOROMETHYL)SULFONYL]-4H-1,3-BENZODIOXIN-2-YL}METHYL)PROPAN-1-AMINE 2-(bromomethyl)-7-[(trifluoromethyl)sulfonyl]-4H-1,3-benzodioxine (1.0 g, 2.77 mmol), propan-1-amine (2.27 ml, 27.7 mmol), potassiumcarbonate (0.57 g, 4.15 mmol) and ACN were heated at 60° C. for 16 h. The volatiles were evaporated and the crude product was purified by flash column chromatography using EtOAc/MeOH (10:1) as eluent, to afford the title product (0.55 g, 58%). The amine (0.30 g) was converted into the hydrochloric acid salt and crystallized from EtOH/DEE. M.p. 201° C. MS m/z (rel. intensity, 70 eV) 339 (M+, 5), 310 (22), 239 (18), 222 (8), 72 (bp).

Example 9

N-{[7-(METHYLSULFONYL)-4H-1,3-BENZODIOXIN-2-YL]METHYL}ETHANAMINE

A mixture of 2-(bromomethyl)-7-(methylsulfonyl)-4H-1,3-benzodioxine (0.40 g, 1.30 mmol), ethanamine (70% in water, 3.0 ml, 37.8 mmol) and ACN (3.0 ml) was heated in a microwave oven at 150° C. for 20 min. The volatiles were evaporated in vacuum. The residue was chromatographed twice on a silica column using EtOAc/MeOH (2:1) as eluent. Collection of the fractions containing pure product and evaporation of the solvent afforded the title compound (0.2 g, 57%). The amine was converted into hydrochloric acid salt and crystallized from EtOH/DEE (0.33 g). The salt was washed with several portions of DEE. M.p. 203° C. $^1$H-NMR (400 MHz, MeOH): δ 7.50 (1H, dd, J1 8, J2 1.6), δ 7.41 (1H, d, J 1.6), δ 7.31 (1H, d, J 8), δ 5.27 (1H, t, J 4.8), δ 5.04 (2H, dd, J1 49, J2 16), δ 3.11 (3H, s), δ 3.01 (2H, t, J 4.0), δ 2.77 (2H, q, J 6.8), δ 1.17 (3H, t, J 7.2).

Example 10

(−)-N-{[7-(METHYLSULFONYL)-4H-1,3-BENZODIOXIN-2-YL]METHYL}ETHANAMINE (−)-N-benzyl-N-{[7-(methylsulfonyl)-4H-1,3-benzodioxin-2-yl]methyl}ethanamine (0.47 g, 1.30 mmol), palladium on carbon (10%, 30 mg) and EtOH (15 ml) was hydrogenated at 50 psi for 13 h. The reaction mixture was filtered through a pad of celite and the filtrate was evaporated to dryness (0.34 g). Purification by flash chromatography (EtOAc/MeOH 4:1) afforded the pure title compound (0.27 g, 77%, >95% e.e.). The amine was converted into the hydrochloric acid salt and crystallized from EtOH/MeOH/DEE. M.p 219° C. $[\alpha]^D_{MeOH}$=−79°. $^1$H-NMR (400 MHz, CDCl$_3$): δ 7.49 (1H, dd, J1 8.0 Hz, J 2 2.0 Hz), δ 7.45 (1H, d, J 2.0 Hz), δ 7.17 (1H, d, J 8.0 Hz), δ 5.19 (1H, t, 4.8 Hz), δ 5.0 (2H, dd, J1 49 Hz, J2 15 Hz), δ 3.03 (3H, s), δ 2.76 (2H, q, J 7.2 Hz), δ 1.46 (1H, s), δ 1.16 (3H, t, J 7.2 Hz).

Example 11

(+)-N-{[7-(METHYLSULFONYL)-4H-1,3-BENZODIOXIN-2-YL]METHYL}ETHANAMINE

Preparation according to Example 10. (+)-N-benzyl-N-{[7-(methylsulfonyl)-4H-1,3-benzodioxin-2-yl]methyl}ethanamine (0.42 g, 1.16 mmol), palladium on carbon (10%, 30 mg) and EtOH (10 ml) was hydrogenated at 50 psi for 7 h. Purification afforded the pure title compound (0.23 g, 73%, >95% e.e). The amine was converted into the hydrochloric acid salt and crystallized from EtOH/MeOH/DEE. M.p. 218° C. $[\alpha]^D_{MeOH}$=+77°. $^1$H-NMR (400 MHz, CDCl$_3$): δ 7.51 (1H, dd, J1 7.6 Hz, J2 1.6 Hz), δ 7.47 (1H, d, J 1.6 Hz), δ 7.19 (1H, d, J 7.6 Hz), δ 5.21 (1H, t, J 5.2 Hz), δ 5.01 (2H, dd, J1 49 Hz, J2 15 Hz), δ 3.05 (3H, s), δ 2.78 (2H, m), δ 1.45 (1H, s), δ 1.80 (3H, t, J 7.2 Hz).

Example 12

N-METHYL-1-[7-(METHYLSULFONYL)-4H-1,3-BENZODIOXIN-2-YL]METHANAMINE

A mixture of 2-(bromomethyl)-7-(methylsulfonyl)-4H-1,3-benzodioxine (0.4 g, 1.30 mmol), methanamine (33% in EtOH, 2.0 ml, 16.1 mmol) and EtOH (3.0 ml) was heated in a micro wave oven at 145° C. for 30 min. The volatiles were evaporated in vacuum and the crude product was chromatographed twice on a silica column using EtOAc/MeOH (4:1) as eluent. Collection of the fractions containing pure product and evaporation of the solvent afforded the title compound (0.25 g, 74%). The amine was converted into hydrochloric acid salt and crystallized from EtOH/MeOH/DEE. M.p. 225° C. MS m/z (rel. intensity, 70 eV) 257 (M+, 1), 123 (76), 78 (35), 77 (bp), 51 (97).

Example 13

(−)-N-METHYL-1-[7-(METHYLSULFONYL)-4H-1,3-BENZODIOXIN-2-YL]METHANAMINE (−)-N-benzyl-N-methyl-1-[7-(methylsulfonyl)-4H-1,3-benzodioxin-2-yl]methanamine (0.37 g, 1.06 mmol), palladium on carbon (10%, 45 mg) and EtOH (15 ml) was hydrogenated at 45 psi for 14 h. The reaction mixture was filtered through a pad of celite and the filtrate was evaporated to dryness (0.25 g). Purification by flash chromatography (EtOAc/MeOH 2:1) afforded the pure title compound (0.23 g, 84%, >95% e.e.). The amine was converted into the hydrochloric acid salt and crystallized from EtOH/MeOH/DEE. M.p. 225° C. $[\alpha]^D_{MeOH}$=−81°. MS m/z (rel. intensity, 70 eV) 257 (M+, 2), 123 (bp), 106 (29), 77 (88), 51 (61).

Example 14

(+)-N-METHYL-1-[7-(METHYLSULFONYL)-4H-1,3-BENZODIOXIN-2-YL]METANAMINE (+)-N-benzyl-N-methyl-1-[7-(methylsulfonyl)-4H-1,3-benzodioxin-2-yl]methanamine (0.37 g, 1.06 mmol), palladium on carbon (10%, 45 mg) and EtOH (20 ml) was hydrogenated at 45 psi for 14 h. Purification by flash chromatography (EtOAc/MeOH 2:1) afforded the pure title compound (0.24 g, 89%, >95% e.e.). The amine was converted into the hydrochloric acid salt and crystallized from EtOH/MeOH/DEE. M.p. 224° C. $[\alpha]^D_{MeOH}$=+77°. $^1$H-NMR (400 MHz, MeOH): δ 7.48 (1h, dd, J1 8.0 Hz, J2 1.6 Hz), δ 7.43 (1H, d, J 2.0 Hz), δ 7.18 (1H, d, J 8.0 Hz), δ 5.19 (1H, t, J 4.8 Hz), δ 5.00 (2H, dd, J 50 Hz, J2 16 Hz), δ 3.03 (3H, s), δ 2.99 (2H, d, J 4.0 Hz), δ 2.53 (3H, s), δ 1.54 (1H, s).

Example 15

N-({7-[(TRIFLUOROMETHYL)SULFONYL]-4H-1,3-BENZODIOXIN-2-YL}METHYL)ETHA-NAMINE

Preparation according to Example 9. 2-(bromomethyl)-7-[(trifluoromethyl)sulfonyl]-4H-1,3-benzodioxine (0.28 g, 0.76 mmol), ethanamine (70% in water, 2.0 ml, 25.2 mmol) and ACN (2.0 ml) was heated at 120° C. for 20 min. Purification by flash chromatography using EtOAc/MeOH (4:1) as eluent afforded the title compound (0.14 g, 52%). The amine was converted into hydrochloric acid salt and crystallized from EtOH/DEE. M.p. 169° C. MS m/z (rel. intensity, 70 eV) 325 (M+, 1), 239 (5), 106 (5), 77 (7), 58 (bp).

Example 16

N-[(7-BROMO-5-FLUORO-4H-1,3-BENZO-DIOXIN-2-YL)METHYL]PROPAN-1-AMINE

Preparation according to Example 3. 7-bromo-2-(bromomethyl)-5-fluoro-4H-1,3-benzodioxine (0.20 g, 0.60 mmol), propan-1-amine (1.0 ml, 12.2 mmol) and EtOH (3.0 ml)was heated at 130° C. for 20 min. Purification by flash column chromatography (EtOAc/MeOH 10:1) gave the title compound (0.15 g, 82%). The amine was converted into the oxalic acid salt and was crystallised with MeOH/DEE (0.17 g). M.p. 215° C. MS m/z (rel. intensity, 70 eV) 304 (M+, 3), 302 (M+, 3), 205 (10), 203 (10), 72 (bp).

Example 17

N-{[5-FLUORO-7-(METHYLSULFONYL)-4H-1,3-BENZODIOXIN-2-YL]METHYL}PROPAN-1-AMINE

A mixture of N-[(7-bromo-5-fluoro-4H-1,3-benzodioxin-2-yl)methyl]propan-1-amine (0.23 g, 0.76 mmol), sodium methanesulfinate (0.14 g, 1.13 mmol, 85%), copperiodide (14 mg, 0.08 mmol), L-proline (17 mg, 0.15 mmol), potassium carbonate (21 mg, 0.15 mmol) in DMSO (2.5 ml) was degassed with nitrogen. Heating in a microwave oven at 140° C. for 30 min afforded product, but the starting material was not completely converted. Additional copperiodide (14 mg, 0.08 mmol) and L-proline (17 mg, 0.15 mmol) were added and the mixture was heated once again at 140° C. for 30 min. The mixture was brought to ambient temperature and EtOAc (100 ml) and water (50 ml) were added. The phases were separated and the aqueous phase was extracted with EtOAc (3×50 ml). The organic phases were combined, dried (Na$_2$SO$_4$), filtered and evaporated. Purification had to be done three times, by flash column chromatography (EtOAc/MeOH 8:1) before affording the pure title compound (90 mg, 39%). The amine was converted into the hydrochloric acid salt and crystallized from EtOH/DEE (55 mg). M.p. 194° C. $^1$H-NMR (400 MHz, MeOH): δ 7.36 (2H, m), δ 5.26 (1H, t, J 4.8 Hz), δ 5.05 (2H, dd, J1 20.8 Hz, J2 16.0 Hz), δ 3.13 (3H, s), δ 2.99 (2H, m), δ 2.66 (2H, t, J 7.6 Hz), δ 1.56 (2H, m), δ 0.95 (3H, t, J 7.6 Hz).

Example 18

1-[5-FLUORO-7-(METHYLSULFONYL)-4H-1,3-BENZODIOXIN-2-YL]-N-METHYLMETHA-NAMINE

Preparation according to Example 17 with a small alteration, no base used. 1-(7-bromo-5-fluoro-4H-1,3-benzodioxin-2-yl)-N-methylmethanamine (0.33 g, 1.2 mmol), sodium methanesulfinate (0.18 g, 1.49 mmol, 85%), copperiodide (23 mg, 0.12 mmol), L-proline (69 mg, 0.60 mmol) and DMSO (6.0 ml) was heated at 140° C. for 45 min. Purification by flash column chromatography (EtOAc/MeOH 4:1) afforded the title compound (30 mg, 10%). The amine was converted into the hydrochloric acid salt and crystallized from MeOH/EtOH/DEE. The crystals were washed thoroughly with DEE. M.p. 234° C. $^1$H-NMR (400 MHz, MeOH): δ 7.28 (2H, m), δ 5.26 (1H, t, J 4.8 Hz), δ 5.05 (2H, dd, J1 20.4 Hz, J2 16.0 Hz), δ 3.13 (3H, s), δ 2.95 (2H, m), δ 2.47 (3H, s).

Example 19

N-[(7-BROMO-6-FLUORO-4H-1,3-BENZO-DIOXIN-2-YL)METHYL]PROPAN-1-AMINE

Preparation according to Example 3. 7-bromo-2-(bromomethyl)-6-fluoro-4H-1,3-benzodioxine (0.60 g, 1.84 mmol), propan-1-amine (1.0 ml, 12.2 mmol) and EtOH (3.0 ml) was Heated at 130° C. for 40 min. Twice purification by flash column chroma-tography (EtOAc) gave the pure title compound (0.23 g, 41%). The amine was converted into the hydrochloric acid salt and crystallized from EtOH/DEE. M.p. 182° C. MS m/z (rel. intensity, 70 eV) 305 (M+, 3), 303 (M+, 3), 205 (8), 203 (8), 96 (6), 95 (10), 72 (bp).

Example 20

N-{[6-FLUORO-7-(METHYLSULFONYL)-4H-1,3-BENZODIOXIN-2-YL]METHYL}PROPAN-1-AMINE

Preparation according to Example 18. N-[(7-bromo-6-fluoro-4H-1,3-benzodioxin-2-yl)methyl]propan-1-amine (0.30 g, 0.99 mmol), sodium methanesulfinate (0.15 g, 1.23 mmol, 85%), copperiodide (19 mg, 0.10 mmol), L-proline (56 mg, 0.49 mmol) and DMSO (6 ml) was heated at 140° C. for 1 h. Purification was made twice by flash column chromatography (ETOAc/MeOH 10:1) and afforded the title compound (135 mg, 45%). The amine was converted into the hydrochloric acid salt and crystallized from EtOH/DEE. M.p. 225° C. $^1$H-NMR (400 MHz, MeOH): δ 7.34 (1H, d, J 6.0 Hz), δ 7.13 (1H, d, J 9.6 Hz), δ 5.21 (1H, t, J 4.8 Hz), δ 5.02 (2H, dd, J1 45.2 Hz, J2 15.6 Hz), δ 3.23 (3H, s), δ 2.96 (2H, m), δ 2.64 (2H, t, J 7.6 Hz), δ 1.56 (2H, m), δ 0.95 (3H, t, J 7.2 Hz).

Example 21

1-{[7-(METHYLSULFONYL)-4H-1,3-BENZO-DIOXIN-2-YL]METHYL}PIPERIDINE

A mixture of 2-(bromomethyl)-7-(methylsulfonyl)-4H-1,3-benzodioxine (0.70 g, 2.28 mmol), piperidine (2.0 ml, 20.2 mmol) and EtOH (4.0 ml) was heated under microwave irradiation at 130° C. for 30 min. The volatiles were evaporated in vacuum and the crude product was chromatographed twice on a silica column using EtOAc as eluent. Collection of the fractions containing pure product and evaporation of the solvent afforded the pure title compound (0.31 g, 49%). The amine was converted into HCl salt and crystallized from MeOH/DEE (0.33 g). M.p. 217° C. $^1$H-NMR (400 MHz, MeOH): δ 7.49 (1H, dd, J1 8.0 Hz, J2 2.0 Hz), δ 7.39 (1H, d, J 1.6 Hz), δ 7.31 (1H, d, J 8.0 Hz), δ 5.31 (1H, t, J 5.2 Hz), δ 5.02 (2H, dd, J1 60.4 Hz, J2 15.6 Hz), δ 3.10 (3H, s), δ 2.77 (2H, m), δ 2.60 (4H, s, broad), δ 1.63 (4H, m), δ 1.49 (2H, m).

Example 22

N-{[7-(METHYLSULFONYL)-4H-1,3-BENZO-DIOXIN-2-YL]METHYL}BUTAN-1-AMINE

A mixture of 2-(bromomethyl)-7-(methylsulfonyl)-4H-1,3-benzodioxine (30 mg, 0.10 mmol), n-butan-1-amine (0.50 ml, 5.1 mmol) and EtOH (1.0 ml) was heated under microwave radiation at 130° C. for 30 min. MS m/z (rel. intensity, 70 eV) 299 (M+, 1), 123 (8), 86 (bp), 77 (9), 72 (10).

Example 23

2-({[7-(METHYLSULFONYL)-4H-1,3-BENZO-DIOXIN-2-YL]METHYL}AMINO)ETHANOL

Preparation according to Example 22 using 2-(bromomethyl)-7-(methylsulfonyl)-4H-1,3-benzodioxine (30 mg, 0.10 mmol), 2-aminoethanol (0.5 ml, 24.9 mmol) and EtOH (1.0 ml). $^1$H-NMR (400 MHz, MeOH): δ 7.51 (1H, dd, J1 8.0 Hz, J2 1.6 Hz), δ 7.41 (1H, d, J 1.2 Hz), δ 7.32 (1H, d, J 8.0 Hz), δ 5.27 (1H, t, J 4.8 Hz), δ 5.09 (2H, dd, J1 50.0 Hz, J2 15.6 Hz), δ 3.68 (2H, t, J 5.6 Hz), δ 3.11 (3H, s), δ 3.02 (2H, t, J 4.0 Hz), δ 2.82 (2H, t, J 5.6 Hz).

Example 24

N-{[7-(METHYLSULFONYL)-4H-1,3-BENZO-DIOXIN-2-YL]METHYL}-N,N-PROPYLPROPAN-1-AMINE

Preparation according to Example 22 using 2-(bromomethyl)-7-(methylsulfonyl)-4H-1,3-benzodioxine (30 mg, 0.10 mmol), N-propylpropan-1-amine (0.50 ml, 3.7 mmol) and EtOH (1.0 ml). MS m/z (rel. intensity, 70 eV) 327 (M+, 1), 115 (8), 114 (bp), 86 (8), 72 (5).

Example 25

N-ETHYL-N-{[7-(METHYLSULFONYL)-4H-1,3-BENZODIOXIN-2-YL]METHYL}-N-PROPAN-1-AMINE

Preparation according to Example 22 using 2-(bromomethyl)-7-(methylsulfonyl)-4H-1,3-benzodioxine (30 mg, 0.10 mmol), N-ethylpropan-1-amine (0.50 ml, 4.3 mmol) and EtOH (1.0 ml). MS m/z (rel. intensity, 70 eV) 313 (M+, 1), 101 (7), 100 (bp), 72 (9), 58 (12).

Example 26

N-{[7-(METHYLSULFONYL)-4H-1,3-BENZO-DIOXIN-2-YL]METHYL}PROP-2-EN-1-AMINE

Preparation according to Example 22 using 2-(bromomethyl)-7-(methylsulfonyl)-4H-1,3-benzodioxine (30 mg, 0.10 mmol), prop-2-en-1-amine (0.50 ml, 6.7 mmol) and EtOH (1.0 ml). MS m/z (rel. intensity, 70 eV) 283 (M+, 1), 123 (6), 77 (7), 71 (5), 70 (bp).

Example 27

N,N-DIMETHYL-1-[7-(METHYLSULFONYL)-4H-1,3-BENZODIOXIN-2-YL]METHANAMINE

Preparation according to Example 22 using 2-(bromomethyl)-7-(methylsulfonyl)-4H-1,3-benzodioxine (30 mg, 0.10 mmol), N-methylmethanamine (2.0 M in MeOH, 0.50 ml, 1.0 mmol) and EtOH (1.0 ml). MS m/z (rel. intensity, 70 eV) 271 (M+, 1), 77 (4), 59 (4), 58 (bp), 51 (3).

Example 28

N-METHYL-N-{[7-(METHYLSULFONYL)-4H-1,3-BENZODIOXIN-2-YL]METHYL}PROPAN-1-AMINE

Preparation according to Example 22 using 2-(bromomethyl)-7-(methylsulfonyl)-4H-1,3-benzodioxine (30 mg, 0.10 mmol), N-methylpropan-1-amine (0.50 ml, 4.9 mmol) and EtOH (1.0 ml). MS m/z (rel. intensity, 70 eV) 299 (M+, 1), 87 (6), 86 (bp), 77 (4), 58 (8).

Example 29

1-{[7-(METHYLSULFONYL)-4H-1,3-BENZO-DIOXIN-2-YL]METHYL}AZETIDINE

Preparation according to Example 22 using 2-(bromomethyl)-7-(methylsulfonyl)-4H-1,3-benzodioxine (30 mg, 0.10 mmol), azetidine (0.10 ml, 1.5 mmol) and EtOH (1.0 ml). MS m/z (rel. intensity, 70 eV) 283 (M+, 1), 123 (4), 77 (6), 71 (5), 70 (bp).

Example 30

4-{[7-(METHYLSULFONYL)-4H-1,3-BENZO-DIOXIN-2-YL]METHYL}MORPHOLINE

Preparation according to Example 22 using 2-(bromomethyl)-7-(methylsulfonyl)-4H-1,3-benzodioxine (30 mg, 0.10 mmol), morpholine (0.50 ml, 5.7 mmol) and EtOH (1.0 ml). MS m/z (rel. intensity, 70 eV) 313 (M+, 1), 101 (6), 100 (bp), 77 (4), 56 (6).

Example 31

2-METHOXY-N-{[7-(METHYLSULFONYL)-4H-1,3-BENZODIOXIN-2-YL]METHYL}ETHANAMINE

Preparation according to Example 22 using 2-(bromomethyl)-7-(methylsulfonyl)-4H-1,3-benzodioxine (30 mg, 0.10 mmol), 2-methyoxyethanamine (0.50 ml, 5.8 mmol) and EtOH (1.0 ml). MS m/z (rel. intensity, 70 eV) 301 (M+, 1), 123 (13), 88 (bp), 72 (25), 56 (13).

Example 32

N-ETHYL-N-{[7-(METHYLSULFONYL)-4H-1,3-BENZODIOXIN-2-YL]METHYL}ETHANAMINE

Preparation according to Example 22 using 2-(bromomethyl)-7-(methylsulfonyl)-4H-1,3-benzodioxine (30 mg, 0.10 mmol), N-ethylethanamine (0.50 ml, 4.8 mmol) and EtOH (1.0 ml). MS m/z (rel. intensity, 70 eV) 299 (M+, 1), 87 (6), 86 (bp), 77 (4), 58 (6).

Example 33

N-METHYL-N-{[7-(METHYLSULFONYL)-4H-1,3-BENZODIOXIN-2-YL]METHYL}ETHANAMINE

Preparation according to Example 22 using 2-(bromomethyl)-7-(methylsulfonyl)-4H-1,3-benzodioxine (30 mg, 0.10 mmol), N-methylethanamine (0.50 ml, 5.8 mmol) and EtOH (1.0 ml). MS m/z (rel. intensity, 70 eV) 285 (M+, 1), 77 (4), 73 (5), 72 (bp), 51 (3).

Example 34

N-{[5-FLUORO-7-(METHYLSULFONYL)-4H-1,3-BENZODIOXIN-2-YL]METHYL}ETHANAMINE

A mixture of 2-(bromomethyl)-5-fluoro-7-(methylsulfonyl)-4H-1,3-benzodioxine (7 mg, 0.021 mmol), ethanamine (0.5 ml, 2 M in MeOH) and EtOH (3 ml) was heated under microwave radiation at 130° C. for 30 min. MS m/z (rel. intensity, 70 eV) 289 (M+, 0.3), 176 (7), 141 (8), 95 (9), 75 (10), 58 (bp).

Example 35

1-{[5-FLUORO-7-(METHYLSULFONYL)-4H-1,3-BENZODIOXIN-2-YL]METHYL}PIPERIDINE

Preparation according to Example 34 using 2-(bromomethyl)-5-fluoro-7-(methylsulfonyl)-4H-1,3-benzodioxine (7 mg, 0.021 mmol), piperidine (0.5 ml) and EtOH (3 ml). MS m/z (rel. intensity, 70 eV) 329 (M+, 0.6), 99 (8), 98 (bp), 95 (4), 70 (4), 55 (6).

Example 36

N-{[5-FLUORO-7-(METHYLSULFONYL)-4H-1,3-BENZODIOXIN-2-YL]METHYL}-2-METHYL-PROPAN-1-AMINE

Preparation according to Example 34 using 2-(bromomethyl)-5-fluoro-7-(methylsulfonyl)-4H-1,3-benzodioxine (7 mg, 0.021 mmol), 2-methylpropan-1-amine (0.5 ml) and EtOH (3 ml). MS m/z (rel. intensity, 70 eV) 317 (M+, 0.4), 274 (11), 141 (15), 86 (bp), 72 (29), 57 (14).

Example 37

N-{[5-FLUORO-7-(METHYLSULFONYL)-4H-1,3-BENZODIOXIN-2-YL]METHYL}BUTAN-1-AMINE

Preparation according to Example 34 using 2-(bromomethyl)-5-fluoro-7-(methylsulfonyl)-4H-1,3-benzodioxine (7 mg, 0.021 mmol), butane-1-amine (0.5 ml) and EtOH (3 ml). MS m/z (rel. intensity, 70 eV) 317 (M+, 0.3), 141 (11), 95 (11), 86 (bp), 72 (13), 57 (9).

Example 38

1-{[5-FLUORO-7-(METHYLSULFONYL)-4H-1,3-BENZODIOXIN-2-YL]METHYL}PYRROLIDINE

Preparation according to Example 34 using 2-(bromomethyl)-5-fluoro-7-(methylsulfonyl)-4H-1,3-benzodioxine (7 mg, 0.021 mmol), pyrrolidine (0.5 ml) and EtOH (1.0 ml). MS m/z (rel. intensity, 70 eV) 315 (M+, 0.5), 95 (4), 85 (6), 84 (bp), 75 (4), 55 (7).

Example 39

N-{[5-FLUORO-7-(METHYLSULFONYL)-4H-1,3-BENZODIOXIN-2-YL]METHYL}PROP-2-EN-1-AMINE

Preparation according to Example 34 using 2-(bromomethyl)-5-fluoro-7-(methylsulfonyl)-4H-1,3-benzodioxine (7 mg, 0.021 mmol), prop-2-en-1-amine (0.5 ml) and EtOH (3 ml). MS m/z (rel. intensity, 70 eV) 301 (M+, 0.4), 141 (9), 95 (8), 75 (8), 71 (6), 70 (bp).

Example 40

N-{[5-FLUORO-7-(METHYLSULFONYL)-4H-1,3-BENZODIOXIN-2-YL]METHYL}-N-PROPYL-PROPAN-1-AMINE

Preparation according to Example 34 using 2-(bromomethyl)-5-fluoro-7-(methylsulfonyl)-4H-1,3-benzodioxine (7 mg, 0.021 mmol), N-propylpropan-1-amine (0.5 ml) and EtOH (3 ml). MS m/z (rel. intensity, 70 eV) 345 (M+, 0.3), 115 (9), 114 (bp), 95 (5), 86 (14), 72 (6).

Example 41

1-[5-FLUORO-7-(METHYLSULFONYL)-4H-1,3-BENZODIOXIN-2-YL]-N,N-DIMETHYLMETHA-NAMINE

Preparation according to Example 34 using 2-(bromomethyl)-5-fluoro-7-(methylsulfonyl)-4H-1,3-benzodioxine (7 mg, 0.021 mmol), N-methylmethanamine (2.0 M in MeOH, 0.5 ml) and EtOH (3 ml). MS m/z (rel. intensity, 70 eV) 289 (M+, 0.2), 141 (2), 95 (4), 75 (5), 59 (4), 58 (bp).

Example 42

N-ETHYL-N-{[5-FLUORO-7-(METHYLSULFONYL)-4H-1,3-BENZODIOXIN-2-YL]METHYL}ETHANAMINE

Preparation according to Example 34 using 2-(bromomethyl)-5-fluoro-7-(methylsulfonyl)-4H-1,3-benzodioxine (7 mg, 0.021 mmol), N-ethylethanamine (0.5 ml) and EtOH (3 ml). MS m/z (rel. intensity, 70 eV) 317 (M+, 0.3), 95 (4), 87 (6), 86 (bp), 75 (4), 58 (7).

Example 43

N-{[5-FLUORO-7-(METHYLSULFONYL)-4H-1,3-BENZODIOXIN-2-YL]METHYL}PROPAN-2-AMINE

Preparation according to Example 34 using 2-(bromomethyl)-5-fluoro-7-(methylsulfonyl)-4H-1,3-benzodioxine (8.5 mg, 0.026 mmol), propan-2-amine (0.5 ml) and EtOH (3 ml). MS m/z (rel. intensity, 70 eV) 303 (M+, 0.3), 95 (10), 86 (14), 75 (8), 72 (bp), 58 (9).

Example 44

N-{[5-FLUORO-7-(METHYLSULFONYL)-4H-1,3-BENZODIOXIN-2-YL]METHYL}-N-METHYL-PROPAN-1-AMINE

Preparation according to Example 34 using 2-(bromomethyl)-5-fluoro-7-(methylsulfonyl)-4H-1,3-benzodioxine (8.5 mg, 0.026 mmol), N-methylpropan-1-amine (0.50 ml) and EtOH (3 ml). MS m/z (rel. intensity, 70 eV) 317 (M+, 0.3), 95 (5), 87 (6), 86 (bp), 75 (5), 58 (15).

Example 45

N-ETHYL-N-{[5-FLUORO-7-(METHYLSULFONYL)-4H-1,3-BENZODIOXIN-2-YL]METHYL}PROPAN-1-AMINE

Preparation according to Example 34 using 2-(bromomethyl)-5-fluoro-7-(methylsulfonyl)-4H-1,3-benzodioxine (8.5 mg, 0.026 mmol), N-ethylpropan-1-amine (0.5 ml) and EtOH (3 ml). MS m/z (rel. intensity, 70 eV) 331 (M+, 0.1), 101 (7), 100 (bp), 95 (5), 72 (14), 58 (12).

Example 46

N-{[5-FLUORO-7-(METHYLSULFONYL)-4H-1,3-BENZODIOXIN-2-YL]METHYL}-N-METHYL-ETHANAMINE

Preparation according to Example 34 using 2-(bromomethyl)-5-fluoro-7-(methylsulfonyl)-4H-1,3-benzodioxine (8.5 mg, 0.026 mmol), N-methylethanamine (0.5 ml) and EtOH (3 ml). MS m/z (rel. intensity, 70 eV) 303 (M+, 0.2), 95 (5), 75 (5), 73 (5), 72 (bp), 58 (3).

Example 47

N-{[5-FLUORO-7-(METHYLSULFONYL)-4H-1,3-BENZODIOXIN-2-YL]METHYL}-2-METHOXYETHANAMINE

Preparation according to Example 34 using 2-(bromomethyl)-5-fluoro-7-(methylsulfonyl)-4H-1,3-benzodioxine (8.5 mg, 0.026 mmol), 2-methyoxyethanamine (0.50 ml) and EtOH (3 ml). MS m/z (rel. intensity, 70 eV) 319 (M+, 0.3), 141 (17), 88 (bp), 72 (29), 58 (12), 56 (16).

Example 48

1-{[5-FLUORO-7-(METHYLSULFONYL)-4H-1,3-BENZODIOXIN-2-YL]METHYL}AZETIDINE

Preparation according to Example 34 using 2-(bromomethyl)-5-fluoro-7-(methylsulfonyl)-4H-1,3-benzodioxine (8.5 mg, 0.026 mmol), azetidine (0.1 ml) and EtOH (3 ml). MS m/z (rel. intensity, 70 eV) 301 (M+, 2), 141 (7), 95 (7), 75 (7), 71 (6), 70 (bp).

Example 49

N-{[5-FLUORO-7-(METHYLSULFONYL)-4H-1,3-BENZODIOXIN-2-YL]METHYL}-2,2-DIMETHYLPROPAN-1-AMINE

Preparation according to Example 34 using 2-(bromomethyl)-5-fluoro-7-(methylsulfonyl)-4H-1,3-benzodioxine (8.5 mg, 0.026 mmol), 2,2-dimethylpropan-1-amine (0.5 ml) and EtOH (3 ml). MS m/z (rel. intensity, 70 eV) 331 (M+, 1), 274 (74), 203 (20), 141 (32), 100 (bp), 72 (74).

Example 50

3-FLUORO-N-{[5-FLUORO-7-(METHYLSULFONYL)-4H-1,3-BENZODIOXIN-2-YL]METHYL}PROPAN-1-AMINE

3-Fluoropropan-1-amine HCl-salt (0.178 g, 1.52 mmol) was basified on a SCX-3 ion exchange column (TEA/MeOH). 2-(bromomethyl)-5-fluoro-7-(methylsulfonyl)-4H-1,3-benzodioxine (8.5 mg, 0.026 mmol) and 3-fluoropropan-1-amine (0.15 M in MeOH/TEA:4/1, 5 ml) was heated under microwave radiation at 120° C. for 1 h 20 min. ESIMS: m/z 322 (M+H)+.

Preparations

Preparation 1

2-(HYDROXYMETHYL)-5-(TRIFLUOROMETHYL)PHENOL

To a solution of 2-hydroxy-4-(trifluoromethyl)benzoic acid (5.0 g, 24.3 mmol) in dry DEE (150 ml), under nitrogen atmosphere, lithium aluminium hydride (1.11 g, 29.2 mmol) was added in portions. The reaction mixture was stirred for 12 h at ambient temperature and then quenched with water and NaOH (5 M). Aqueous HCl (10%) was added and the aqueous phase was extracted with EtOAc. The combined organic phases were dried (Na$_2$SO$_4$), filtered and evaporated to dryness. The residue was purified by flash column chromatography (isooctane/EtOAc 1:1) to give the title compound (2.55 g). MS m/z (rel. intensity, 70 eV) 192 (M+, 32), 174 (45), 146 (bp), 145 (62), 96 (54).

Preparation 2

2-(CHLOROMETHYL)-7-(TRIFLUOROMETHYL)-4H-1,3-BENZODIOXINE 2-(hydroxymethyl)-5-(trifluoromethyl)phenol (1.0 g, 5.2 mmol) was dissolved in AcOH (4 ml) and cooled on ice-bath. Chloroacetaldehyde (0.93 ml, 7.3 mmol) and concentrated HCl (1.0 ml) were consecutively added drop wise. After 24 h, further addition of chloroacetaldehyde (0.50 ml, 3.9 mmol) and concentrated HCl (1.0 ml) were done and the reaction mixture was allowed to stir another 24 h. Water was added and the aqueous phase was extracted with EtOAc. The combined organic phases were dried (Na$_2$SO$_4$) and evaporated under reduced pressure to give an oil. Twice purification by flash column chromatography (isooctane/EtOAc 4:1) gave the pure title compound (0.08 g, 6%). MS m/z (rel. intensity, 70 eV) 252 (M+, 10), 174 (76), 146 (bp), 145 (47), 127 (44).

Preparation 3

1-(4-FLUORO-2-METHOXYPHENYL)ETHANONE 1-(4-fluoro-2-hydroxyphenyl)ethanone (12.0 g, 77.9 mmol), iodomethane (6.38 ml, 101 mmol), potassiumcarbonate (14.0 g, 101 mmol) were heated at 75° C. in ACN (200 ml) for 8 h. The reaction mixture was brought to ambient temperature, filtered and then evaporated under reduced pressure to dryness. New ACN (150 ml), iodomethane (2 ml, 32 mmol) and potassiumcarbonate (4 g, 29 mmol) was added. The reaction mixture was heated at 75° C. for 3 h. The reaction mixture was concentrated, EtOAc (100 ml) was added and the mixture was filtered and evaporated to give the title product (13.5 g, 100%). MS m/z (rel. intensity, 70 eV) 168 (M+, 11), 153 (bp), 110 (23), 95 (21), 82 (12).

Preparation 4

1-[2-METHOXY-4-(METHYLTHIO)PHENYL]ETHANONE

Sodium thiomethoxide (3.35 g, 47.8 mmol) was dissolved in dry DMF (35 ml) under a blanket of nitrogen. The solution was cooled to −15° C. and 1-(4-fluoro-2-methoxyphenyl)ethanone (6.7 g, 39.8 mmol) was added in portions. After 10 min at −15° C. the reaction mixture was brought to 0° C. for 1.5 h. EtOAc was added and the organic phase was washed three times with aqueous HCl (10%), dried ($Na_2SO_4$) and evaporated under reduced pressure to dryness. Purification by flash column chromatography (isooctane/EtOAc 4:1) gave the pure title compound (6.3 g, 81%). MS m/z (rel. intensity, 70 eV) 196 (M+, 37), 182 (11), 181 (bp), 166 (7), 138 (10).

Preparation 5

2-METHOXY-4-(METHYLTHIO)BENZOIC ACID

Sodiumhydroxide (11.0 g, 275 mmol) was dissolved in water (70 ml) and cooled to 0° C. Bromine (3.5 ml, 68.7 mmol) was added, and after 15 min a cold solution of 1-[2-methoxy-4-(methylthio)phenyl]ethanone in dioxane (140 ml) was added dropwise during 20 min. The reaction mixture was stirred at 0° C. for 2.5 h. $Na_2SO_3$ (10 g dissolved in 50 ml water) was added and after 10 min the reaction mixture was acidified with an aqueous HCl (10%). The aqueous phase was extracted with EtOAc and the combined organic phases were dried ($Na_2SO_4$) and evaporated under reduced pressure to give an oil (5.7 g) of the title compound. Some sulfoxide and sulfonyl compound are also observed. $^1$H-NMR (400 MHz, MeOH): δ 7.77 (1H, d, J 8.4 Hz), δ 6.91 (1H, s), δ 6.84 (1H, dd, J1 8.0 Hz, J2 1.2 Hz), δ 3.96 (3H, s), δ 2.53 (3H, s).

Preparation 6

2-METHOXY-4-(METHYLSULFONYL)BENZOIC ACID 2-methoxy-4-(methylthio)benzoic acid (10.8 g, 54 mmol) is dissolved in acetic acid and the solution was cooled to 10° C. Sodium tungstate 2-hydrate (1.2 g, 3.7 mmol) was added until percipitation. After the precipitation had dissolved and the solution was cooled $H_2O_2$ (4.1 ml, 135 mmol) was added dropwise. 10 minutes later the reaction mixture was heated to 50° C. for 1 h. Sodium sulphite (3.4 g, 27 mmol) in water (80 ml) was added and the resulting mixture was stirred for 30 min. Water and aqueous HCl (10%) were added. The aqueous phase was extracted with EtOAc and the combined organic layers were dried ($Na_2SO_4$) and evaporated under reduced pressure to give a white powder (5.7 g). No further purification was made of this intermediate. $^1$H-NMR (400 MHz, MeOH): δ 7.92 (1H, d, J 8 Hz), δ 7.61 (1H, s), δ 7.56 (1H, d, J 8 Hz), δ 3.95 (3H, s), δ 3.18 (3H, s).

Preparation 7

2-HYDROXY-4-(METHYLSULFONYL)BENZOIC ACID

A solution of 1.0 M boron tribromide (44.0 ml, 44.0 mmol) in DCM (20 ml) was cooled to 0° C. 2-methoxy-4-(methylsulfonyl)benzoic acid (4.0 g, 17.4 mmol) dispergated in DCM (120 ml) was slowly added to the tribromide-solution during 20 minutes. The reaction mixture was vigorously stirred for 1.5 h at 0° C. Water was added and the organic phase was separated. The aqueous phase was extracted with DCM and EtOAc. The combined organic phases was dried ($Na_2SO_4$) and evaporated under reduced pressure to give a white powder (3.6 g). $^1$H-NMR (400 MHz, MeOH): δ 8.07 (1H, d, J 8.0 Hz), 7.42 (1H, d, J 2.0 Hz), δ 7.38 (1H, dd, J1 8.4 Hz, J2 1.6 Hz), δ 3.11 (3H, s).

Preparation 8

2-(HYDROXYMETHYL)-5-(METHYLSULFONYL)PHENOL 2-hydroxy-4-(methylsulfonyl)benzoic acid (3.59 g, 16.6 mmol) was dissolved in dry THF (100 ml) under a blanket of nitrogen. The solution was cooled down to 0° C. and 1.0 M borane tetrahydrofuran complex (61.4 ml, 61.4 mmol) was slowly added. After completed addition the reaction mixture was brought to ambient temperature and stirred for 17 h. Then it was cooled once more to 0° C. and carefully quenched with water, acidified with aqueous HCl (5%) and finally extracted several times with EtOAc. The combined organic phases were dried ($Na_2SO_4$), filtered and evaporated to dryness. Since 50% of the starting material remained the reaction was done once more with THF (250 ml) and 1.0 M borane tetrahydrofurane (50 ml, 50 mmol). Same workup as before but prior to extraction the pH was adjusted to 7. The organic phase was dried ($Na_2SO_4$), filtered and evaporated under reduced pressure to give a white powder (3.3 g). $^1$H-NMR (400 MHz, MeOH): δ 7.6 (1H, d, J 8 Hz), δ 7.39 (1H, d, J 8 Hz), δ 7.28 (1H, s), δ 4.69 (2H, s), δ 3.06 (3H, s).

Preparation 9

2-(BROMOMETHYL)-7-(METHYLSULFONYL)-4H-1,3-BENZODIOXINE 2-(hydroxymethyl)-5-(methylsulfonyl)phenol (3.3 g, 16.3 mmol), 2-bromo-1,1-dimethoxyetane (19.0 ml, 163 mmol), dry THF (30 ml) and concentrated $H_2SO_4$ (5 ml) were heated at 55° C. for 1 h. The reaction mixture was brought to ambient temperature and EtOAc and water were added. The phases were separated and the aqueous phase was extracted twice with EtOAc. The combined organic phases were dried ($Na_2SO_4$), filtered and evaporated to dryness to give an oil (9.0 g). The oil was crystallizing upon cooling. The product was washed with EtOAc, EtOH and DEE and afforded the pure title compound (4.0 g, 80%). MS m/z (rel. intensity, 70 eV) 308 (M+, 11), 306 (M+, 10), 213 (45), 184 (bp), 77 (35).

Preparation 10

(−) AND (+)-N-BENZYL-N-{[7-(METHYLSULFONYL)-4H-1,3-BENZODIOXIN-2-YL]METHYL}PROPAN-1-AMINE

N-{[7-(methylsulfonyl)-4H-1,3-benzodioxin-2-yl]methyl}propan-1-amine (1.2 g, 4.2 mmol), benzylbromide (0.53 ml, 4.4 mmol), potassium carbonate (0.70 g, 5.0 mmol) and ACN (50 ml) were heated at 60° C. for 2.5 h. EtOAc (100 ml) was added and the mixture was filtered and evaporated to dryness. Purification by flash chromatography (isooctane/EtOAc 1:1) and evaporation of pure fractions afforded the title compound (1.2 g). $^1$H-NMR (400 MHz, MeOH): δ 7.48 (1H, dd, J1 8.0 Hz, J2 2.0 Hz), δ 7.38-7.21 (7H, m), δ 5.18 (1H, t, J 5.6 Hz), δ 4.97 (2H, dd, J1 41.6 Hz, J2 15.6 Hz), δ 3.77 (2H, q, J 13.6 Hz), δ 3.10 (3H, s), δ 2.94-2.84 (2H, m), δ 2.58 (2H, dt, J1 7.2 Hz, J2 1.6 Hz), δ 1.56 (2H, m), δ 0.90 (2H, t, J 7.2 Hz).

Chiral preparative HPLC (Kromasil 5-CelluCoat Dimensions 21.2×250 mm) of the racemate with a mobile phase consisting of hep/EtOH/DEA (90:10:0.1) was preformed. Flow-rate 20 ml/min and detector wavelength 280 nm. Repeated injections (35-40 mg) every 20 min. Totally 38 injections and collection of the enantiomeric pure fractions of the first and second peak afforded the two different enantiomers. Retention times were 15.2 min and 17.1 min (analytical system). The first eluted peak afforded the (−)-enantiomer (0.52 g, >95% e.e.). $[α]^D_{EtOH}$=−93°. The second eluted peak afforded the (+)-enantiomer (0.43 g, >95% e.e.). $[α]^D_{EtOH}$=+98°.

Preparation 11

2-(CHLOROMETHYL)-7-(METHYLSULFONYL)-4H-1,3-BENZODIOXINE 2-(hydroxymethyl)-5-(methylsulfonyl)phenol (0.2 g, 1.0 mmol) was dissolved in EtOH (4.5 ml) and chloroacetaldehyde (0.15 ml, 1.2 mmol) was added. The mixture was cooled to 0° C. and concentrated $H_2SO_4$ (2.5 ml) was added dropwise. The reaction mixture was stirred at 0° C. for 10 min and then in room temperature for 2-3 h. Chloroacetaldehyde (50 µl) and concentrated $H_2SO_4$ (0.5 ml) was added and the reaction mixture was stirred for another 1-2 h before the reaction was quenched with water. The aqueous phase was extracted with EtOAc and the combined organic phases were dried ($Na_2SO_4$) and evaporated under reduced pressure to give an oil. Purification by flash column chromatography (isooctane/EtOAc 2:1) gave the title compound (0.58 g, with some inpurities). MS m/z (rel. intensity, 70 eV) 264 (M+, 5), 262 (M+, 13), 213 (31), 184 (bp), 77 (61), 51 (47).

Preparation 12

2-PHENYL-7-[(TRIFLUOROMETHYL)THIO]-4H-1,3,2-BENZODIOXABORININ

A mixture of 3-[(trifluoromethyl)thio]phenol (10.0 g, 51.5 mmol), phenylboronic acid (6.91 g, 56.7 mmol), propionic acid (1.92 ml, 25.8 mmol) and paraformaldehyde (1.46 g, 48.7 mmol), and toluene was heated at reflux using a Dean-Stark trap to separate water formed during the reaction. Additional paraformaldehyde was added (3×1 g+7×0.5 g, 0.22 mol) and additional propionic acid was added (2×0.5 ml, 13.4 mmol). The mixture was brought to ambient temperature, quenched with water and extracted with EtOAc. The combined organic layers were washed with $Na_2CO_3$ (10%), dried ($Na_2SO_4$), filtered and evaporated to dryness (14.0 g). MS m/z (rel. intensity, 70 eV) 310 (M+, 41), 309 (19), 242 (11), 241 (bp), 240 (28), 109 (14).

Preparation 13

2-(HYDROXYMETHYL)-5-[(TRIFLUOROMETHYL)THIO]PHENOL

A solution of 2-phenyl-7-[(trifluoromethyl)thio]-4H-1,3,2-benzodioxaborinin (14.0 g, 44 mmol) and $H_2O_2$ (30% in water, 27.0 ml, 264 mmol) in THF (100 ml) was stirred at ambient temperature for 3 h, before it was quenched at 0° C. with a aqueous solution of $Na_2SO_3$ (19.0 g). The mixture was acidified with HCl (10%), extracted with EtOAc and the combined organic layers were evaporated to dryness (no drying agent). The crude product was purified on flash column chromatography (isooctane/EtOAc 4:1 and isooctane/EtOAc 7:3) to afford two different fractions. One fraction with the stereoisomer as a by-product, 2-(hydroxymethyl)-3-[(trifluoromethyl)thio]phenol (4.1 g) and one with the title product (2.75 g). $^1$H-NMR (400 MHz, MeOH): δ 7.40 (1H, d, J 8.0 Hz), δ 7.13 (1H, d, J 8.0 Hz), δ 7.12 (1H, s), δ 4.66 (2H, s).

Preparation 14

2-(HYDROXYMETHYL)-5-[(TRIFLUOROMETHYL)SULFONYL]PHENOL

A mixture of 2-(hydroxymethyl)-5-[(trifluoromethyl)thio]phenol (2.75 g, 12.3 mmol), $H_2O_2$ (3.8 ml, 36.9 mmol), sodium tungstate 2-hydrate (0.50 g, 1.5 mmol) and AcOH (20 ml) was heated at 50° C. for 3 h. The reaction was quenched with $Na_2SO_3$ (8.0 g in water) at 0° C. and then stirred for 10 minutes. Water and EtOAc was added and then the organic phase was washed with water, dried, filtered and concentrated to afford the title product (2.7 g). $^1$H-NMR (400 MHz, MeOH): δ 7.73 (1H, d, J 7.6 Hz), δ 7.53 (1H, d, J 8.4 Hz), δ 7.36 (1H, s), δ 4.73 (2H, s).

Preparation 15

2-(BROMOMETHYL)-7-[(TRIFLUOROMETHYL)SULFONYL]-4H-1,3-BENZODIOXINE

Preparation according to Preparation 9. 2-(hydroxymethyl)-5-[(trifluoromethyl)sulfonyl]phenol (2.7 g, 10.5 mmol), 2-bromo-1,1-dimethoxyethane (3.0 ml, 25.4 mmol), conc. $H_2SO_4$ (1.0 ml), THF (20 ml). Heating at 50° C. for 6 h. Additional 2-bromo-1,1-dimethoxyethane (5×0.5 ml, 21.1 mmol) and conc. $H_2SO_4$ (3×1.0 ml) were added during the reaction. Purification by flash column chromatography gave the title compound (3.3 g). MS m/z (rel. intensity, 70 eV) 362 (M+, 5), 360 (M+, 5), 267 (bp), 238 (64), 141 (52), 77 (55).

Preparation 16

(−) AND (+)-N-BENZYL-N-{[7-(METHYLSULFONYL)-4H-1,3-BENZODIOXIN-2-YL]METHYL}ETHANAMINE

N-{[7-(methylsulfonyl)-4H-1,3-benzodioxin-2-yl]methyl}ethanamine (0.93 g, 3.4 mmol), benzylbromide (0.43 ml, 3.6 mmol), potassium carbonate (0.61 g, 4.4 mmol) and ACN (20 ml) were heated at 70° C. for 2 h. EtOAc (50 ml) was added before the reaction mixture was filtered and concentrated. Purification by flash chromatography (isooctane/EtOAc 1:1) afforded the title compound (1.1 g). $^1$H-NMR (400 MHz, MeOH): δ 7.47 (1H, dd, J1 8 Hz, J2 1.6 Hz), δ 7.31 (7H, m), δ 5.18 (1H, t, J 5.2 Hz), δ 4.97 (2H, dd, J1 41 Hz, J2 15 Hz), δ 3.09 (3H, s), δ 2.90 (2H, m), δ 2.70 (2H, m), δ 1.12 (3H, t, J 7.2 Hz).

Chiral preparative HPLC (Cellucoat) of the racemate with a mobile phase consisting of hep/EtOH/DEA (90:10:0.1) was preformed. The flow-rate was 20 ml/min and detector wavelength 280 nm. Repeated injections (55-60 mg) every 23 min. Totally 23 injections and collection of the enantiomeric pure fractions of the first and second peak afforded the two different enantiomers. The first eluted peak afforded the (−)-N-benzyl-N-{[7-(methylsulfonyl)-4H-1,3-benzodioxin-2-yl]methyl}ethanamine (0.47 g, >95% e.e.). The second eluted peak afforded the (+)-N-benzyl-N-{[7-(methylsulfonyl)-4H-1,3-benzodioxin-2-yl]methyl}ethanamine (0.42 g, >95% e.e.).

Preparation 17

(−)/(+)-N-BENZYL-N-METHYL-1-[7-(METHYLSULFONYL)-4H-1,3-BENZODIOXIN-2-YL]METHANAMINE

N-methyl-1-[7-(methylsulfonyl)-4H-1,3-benzodioxin-2-yl]methanamine (1.05 g, 4.1 mmol), benzylbromide (0.49 ml, 4.1 mmol), potassium carbonate (0.68 g, 4.9 mmol) and ACN (20 ml) were heated at 50° C. for 12 h. EtOAc was added, the reaction mixture was filtered and concentrated. Purification by flash chromatography (isooctane/EtOAc 1:2) afforded the title compound (0.91 g). $^1$H-NMR (400 MHz, MeOH): δ 7.38 (1H, dd, J 8.4 Hz, J2 1.6), δ 7.28-7.14 (7H, m), δ 5.17 (1H, t, J 4.0 Hz), δ 4.90 (2H, dd, J 52.0 Hz, J2 19.6 Hz), δ 3.59 (2H, dd, J 18.4 Hz, J2 13.2 Hz), δ 2.99 (3H, s), δ 2.78-2.67 (2H, m), δ 2.29 (3H, s). Chiral separation was performed according to Preparation 16. The flow rate was 30 ml/min. Repeated injections (~40 mg) every 7-8 min. Totally 25 injections afforded the two different enantiomers. The first eluted peak consisted of (−)-N-benzyl-N-methyl-1-{[7-(methylsulfonyl)-4H-1,3-benzodioxin-2-yl]methanamine (0.37 g, >95% e.e.). The second eluted peak consisted of (+)-N-benzyl-N-methyl-1-{[7-(methylsulfonyl)-4H-1,3-benzodioxin-2-yl]methanamine (0.37 g, >95% e.e.).

Preparation 18

4-BROMO-2,6-DIFLUOROBENZOIC ACID

A solution of n-buthyllithium in hexane (2.5 M, 20.7 ml, 51.8 mmol) in dry THF (100 ml) was cooled down to −78° C. under nitrogen atmosphere. 2,2,6,6-tetramethylpiperidine (8.7 ml, 51.8 mmol) and 1-bromo-3,5-difluorobenzene (10.0 g, 51.8 mmol) were consecutively added. The reaction mixture was stirred for 2 h at −78° C., before it was quenched with an excess of freshly crushed $CO_2$ (s). After 15 min, the mixture was brought to ambient temperature and the solvent was evaporated. The residue was dissolved in water, washed with EtOAc, acidified with aqueous HCl (1.0 M) and extracted with EtOAc. The combined organic phases were dried, filtered and concentrated in vacuo to afford 6.8 g of pure title product. $^1$H-NMR (400 MHz, MeOH): δ 7.27 (2H, d, J 7.6 Hz).

Preparation 19

METHYL 4-BROMO-2,6-DIFLUOROBENZOATE

A mixture of 4-bromo-2,6-difluorobenzoic acid (6.7 g, 28.3 mmol), MeOH (200 ml) and concentrated HCl (2.0 ml) was heated at reflux for 12 h. The reaction mixture was brought to ambient temperature and the volatiles were evaporated. EtOAc was added and the organic phase was extracted with a aqueous solution of $Na_2CO_3$ (10%). The combined alkaline phases was acidified at 0° C. with aqueous HCl (10%) to pH 1 and extracted with EtOAc. The combined organic phases was dried ($Na_2SO_4$), filtered and concentrated in vacuo to afford pure title compound (3.1 g). MS m/z (rel. intensity, 70 eV) 252 (M+, 22), 250 (M+, 23), 221 (99), 219 (bp), 112 (44).

Preparation 20

METHYL 4-BROMO-2-FLUORO-6-HYDROXYBENZOATE

Methyl 4-bromo-2,6-difluorobenzoate (0.5 g, 2.0 mmol), 2-butyn-1-ol (0.16 ml, 2.1 mmol), potassium tertbutoxide (0.47 g, 4.2 mmol) in dry DMSO (5 ml) was heated in a microwave oven at 125° C. for 2.5 min. The reaction mixture was cooled to ambient temperature and quenched with water. The mixture was acidified with aqueous HCl (1 M) and extracted with EtOAc, dried ($Na_2SO_4$), filtered and evaporated to dryness to afford an oil. Purification by flash column chromatography (isooctane/EtOAc 10:1) gave the title compound (0.19 g, 35%). MS m/z (rel. intensity, 70 eV) 250 (M+, 43), 248 (M+, 44), 218 (96), 216 (bp), 190 (44),188 (45).

Preparation 21

5-BROMO-3-FLUORO-2-(HYDROXYMETHYL) PHENOL

Methyl 4-bromo-2-fluoro-6-hydroxybenzoate (0.34 g, 1.4 mmol) was dissolved in dry THF (20 ml) under a blanket of nitrogen. The solution was cooled down to 0° C. and borane tetrahydrofuran complex (5.0 ml, 5.0 mmol) was slowly added. The mixture was stirred at 0° C. for 30 min and at ambient temperature for 15 min. Then it was cooled once more to 0° C. and carefully quenched with water, acidified with aqueous HCl (5%) and finally extracted several times with EtOAc. The combined organic phases were dried ($Na_2SO_4$), filtered and evaporated to dryness (0.33/g) to afford the title compound. No further purification was done on this intermediate. ESIMS: m/z 223 (M+H)$^+$, 221 (M+H)$^+$.

Preparation 22

7-BROMO-2-(BROMOMETHYL)-5-FLUORO-4H-1,3-BENZODIOXINE

Preparation according to Preparation 9. 5-bromo-3-fluoro-2-(hydroxymethyl)phenol (0.79 g, 3.6 mmol), 2-bromo-1,1-dimethoxyethane (4.2 ml, 36 mmol), dry THF (10 ml) and concentrated $H_2SO_4$ (1.5 ml).

Purification by flash column chromatography (isooctane/EtOAc 10:1) gave the title compound (0.52 g, 40%). MS m/z (rel. intensity, 70 eV) 328 (M+, 12), 326 (M+, 24), 324 (M+, 13), 204 (95), 202 (bp), 176 (24), 174 (25), 95 (35).

Preparation 23

1-[(7-BROMO-5-FLUORO-4H-1,3-BENZO-DIOXIN-2-YL)-N-METHYLMETHANAMINE

Preparation according to Example 12. 7-bromo-2-(bromomethyl)-5-fluoro-4H-1,3-benzodioxine (0.50 g, 1.53 mmol), methanamine (2.0 ml, 33% in EtOH) and EtOH (4.0 ml) were heated in a micro wave oven at 120° C. for 1 h 5 min. The volatiles were evaporated in vacuum and the crude product was chromathographed twice on a silica column using EtOAc/MeOH (4:1) as eluent. Collection of the fractions containing pure product and evaporation of the solvent afforded the title compound (0.40 g, 94%). $^1$H-NMR (400 MHz, MeOD): δ 6.93 (2H, m), δ 5.26 (1H, t, J 4.8 Hz), δ 4.93 (2H, dd, J1 18.4 Hz, J2 15.2 Hz), δ 3.02 (2H, m), δ 2.53 (3H, s) ppm.

Preparation 24

4-BROMO-2,5-DIFLUOROBENZOIC ACID

To a solution of 1,4-dibromo-2,5-difluorobenzene (6.4 g, 23.5 mmol) in dry DEE (100 ml), under nitrogen atmosphere, at −78° C. was added dropwise n-butyl lithium (2.5 M in hexane, 9.6 ml, 24.0 mmol). The mixture was stirred for 30 min at −78° C. and then it was quenched with an excess of freshly crushed $CO_2$ (s). After 15 min, the mixture was brought to ambient temperature and water (50 ml) was added. The phases were separated and the organic layer was extracted with $Na_2CO_3$ (10%, 2×50 ml). The aqueous phases were combined, acidified with aqueous HCl (1 M) and extracted with EtOAc (2×100 ml). The combined organic layers were dried ($Na_2SO_4$), filtered and concentrated in vacuo to give 4.81 g of title product. $^1$H-NMR (400 MHz, MeOH): δ 7.70 (1H, dd, J 8.8, 6.4), δ 7.58 (1H, dd, J 9.2, 5.6)

Preparation 25

METHYL 4-BROMO-2,5-DIFLUOROBENZOATE 4-bromo-2,5-difluorobenzoic acid (4.82 g, 20.3 mmol) and methanol (100 ml, saturated with gaseous HCl) was heated at 65° C. for 3 h. The volatiles were evaporated, MeOH was added and once again it was evaporated. This procedure was repeated three times. Purification by flash column chromatography (isooctane/EtOAc 4:1) gave the title compound (4.2 g). MS m/z (rel. intensity, 70 eV) 252 (M+, 33), 250 (M+, 34), 221 (95), 219 (bp), 193 (20), 191 (21), 112 (32).

Preparation 26

METHYL 4-BROMO-5-FLUORO-2-METHOXYBENZOATE

A solution of methyl 4-bromo-2,5-difluorobenzoate (1.0 g, 3.98 mmol) in dry DMF (10 ml) was cooled down to 0° C. Sodium methoxide (25% in MeOH, 0.91 ml, 3.98 mmol) was dried with activated molecular sieves and slowly added to the starting material. The reaction mixture was stirred at 0° C. for 10 min and then at ambient temperature for 30 min. The mixture was then brought back to 0° C. and quenched with EtOAc (50 ml) and aqueous HCl (1 M, 50 ml). The phases were separated and the aqueous phase was extracted with EtOAc (2×100 ml), dried ($Na_2SO_4$), filtered and evaporated to give an oil. The crude product was purified by flash column chromatography (isooctane/EtOAc 9:1) gave the title compound (0.81 g, 75%). MS m/z (rel. intensity, 70 eV) 264 (M+, 30), 262 (M+, 31), 233 (65), 231 (bp), 229 (41).

Preparation 27

METHYL 4-BROMO-5-FLUORO-2-HYDROXYBENZOATE

Preparation according to Preparation 7, using boron tribromide (1.0 M, 25.0 ml, 25.2 mmol) in DCM (25 ml) and methyl 4-bromo-5-fluoro-2-methoxybenzoate (2.2 g, 8.4 mmol) in DCM (15 ml). Yield: 2.1 g. MS m/z (rel. intensity, 70 eV) 250 (M+, 40), 248 (M+, 41), 218 (99), 216 (bp), 188 (41), 186 (41), 81 (39).

Preparation 28

5-BROMO-4-FLUORO-2-(HYDROXYMETHYL) PHENOL

Preparation according to Preparation 21, using methyl 4-bromo-5-fluoro-2-hydroxybenzoate (2.1 g, 8.4 mmol), borane tetrahydrofuran complex (31.0 ml, 31.0 mmol) and dry THF. Yield: 3.3 g (not pure). ESIMS: m/z 221 (M+H)$^+$, 219 (M+H)$^+$.

Preparation 29

7-BROMO-2-(BROMOMETHYL)-6-FLUORO-4H-1,3-BENZODIOXINE

Preparation according to Preparation 9. 5-bromo-4-fluoro-2-(hydroxymethyl)phenol (2.3 g, 10.4 mmol), 2-bromo-1,1-dimethoxyethane (9.9 ml, 83 mmol), dry THF (30 ml) and concentrated $H_2SO_4$ (4 ml) were heated at 55° C. for 2 h. Purification by flash column chromatography (isooctane/ EtOAc 10:1) gave the title compound (1.55 g). MS m/z (rel. intensity, 70 eV) 328 (M+, 11), 326 (M+, 23), 324 (M+, 12) 204 (98), 202 (bp), 176 (41), 174 (43), 95 (59).

Preparation 30

METHYL 2-FLUORO-6-HYDROXY-4-(METHYLSULFONYL) BENZOATE

Methyl 4-bromo-2-fluoro-6-hydroxybenzoate (1.7 g, 5.6 mmol), sodium methanesulfinate (95%) (0.91 g, 8.5 mmol), CuI (0.64 g, 3.4 mmol), L-proline (0.78 g, 6.8 mmol) and $K_2CO_3$ (0.47 g, 3.4 mmol) was dissolved in DMSO (dry) (10 ml). Nitrogen was bubbled through the solution for 15 min. The mixture was stirred and heated at 95° C. for 6 h under nitrogen. After cooling to RT, the mixture was filtered on a plug of silica and eluted with ETOAc. The filtrate was washed with 1M citric acid. The waterlayer was extracted once with EtOAc. The combined organic phases were washed with brine, dried ($Na_2SO_4$), filtered and concentrated. Purification on flash column chromatography (isooctane/EtOAc) gave the crude title compound (0.14 g). MS m/z (rel. intensity, 70 eV) 248 (M+, 36), 216 (bp), 173 (19), 125 (20), 81 (24).

Preparation 31

3-FLUORO-2-(HYDROXYMETHYL)-5-(METH-YLSULFONYL)PHENOL

Methyl 2-fluoro-6-hydroxy-4-(methylsulfonyl)benzoate (0.14 g, 0.57 mmol) was dissolved in THF (dry) (5 ml).

LiBH$_4$ (2M in THF) (0.57 ml, 1.14 mmol) was added dropwise under nitrogen at 0° C. The mixture was allowed to warm to RT and stirred under nitrogen for 45 min. EtOAc was added and the mixture was further quenched with MeOH, then water. The mixture was acidified with 1N HCl and extracted with EtOAc. The combined extracts were washed with brine, dried (Na$_2$SO$_4$) and concentrated to give the crude title compound (0.12 g) $^1$H-NMR (400 MHz, CD$_3$OD): δ 7.20 (1H, s), 7.16 (1H, dd, J 8.4, 2), δ 4.73 (2H, d, J 1.6), δ 3.10 (3H, s) ppm (J-values are in Hz and shifts relative to solvent-peak at 3.31 ppm).

Preparation 32

2-(BROMOMETHYL)-5-FLUORO-7-(METHYL-SULFONYL)-4H-1,3-BENZODIOXINE 3-fluoro-2-(hydroxymethyl)-5-(methylsulfonyl)phenol (0.11 g, 0.52 mmol) was dissolved in THF (dry) (5 ml). 2-bromo-1,1-dimethoxyethane (0.63 ml, 5.2 mmol) was added followed by concentrated H$_2$SO$_4$ (1 ml). The mixture was heated at 60° C. for 1 h. Water was added and the mixture extracted with EtOAc twice. The combined extracts were washed with brine and concentrated. Purification by flash column chromatography (isooctane/EtOAc) gave the title compound (0.073 g). MS m/z (rel. intensity, 70 eV) 326 (M+, 8), 324 (M+, 8), 231 (17), 202 (bp), 139 (21), 95 (42), 75 (34).
Biological Activity The following tests are used for evaluation of the compounds according to the invention.
In Vivo Test: Behaviour Behavioural activity is measured using eight Digiscan activity monitors (RXYZM (16) TAO, Omnitech Electronics, Columbus, Ohio, USA), connected to an Omnitech Digiscan analyzer and an Apple Macintosh computer equipped with a digital interface board (NB DIO-24, National Instruments, USA). Each activity monitor consists of a quadratic metal frame (W×L=40 cm×40 cm) equipped with photobeam sensors. During measurements of behavioural activity, a rat is put in a transparent acrylic cage (W×L×H, 40×40×30 cm) which in turn was placed in the activity monitor. Each activity monitor is equipped with three rows of infrared photobeam sensors, each row consisting of 16 sensors. Two rows are placed along the front and the side of the floor of the cage, at a 90° angle, and the third row is placed 10 cm above the floor to measure vertical activity. Photobeam sensors are spaced 2.5 cm apart. Each activity monitor is fitted in an identical sound and light attenuating box containing a weak house light and a fan.

The computer software is written using object oriented programming (LabVIEW®, National instruments, Austin, Tex., USA).

Behavioural data from each activity monitor, representing the position (horizontal center of gravity and vertical activity) of the animal at each time, are recorded at a sampling frequency of 25 Hz and collected using a custom written LABView™ application. The data from each recording session are stored and analyzed with respect to distance traveled. Each behavioural recording session lasts 60 min, starting approximately 4 min after the injection of test compound. Similar behavioural recording procedures are applied for drug-naïve and drug pre-treated rats. Rats pre-treated with d-amphetamine are given a dose of 1.5 mg/kg i.p. 10 min before the recording session in the activity monitor. Rats pre-treated with MK-801 are given a dose of 0.7 mg/kg i.p. 90 min before the recording session in the activity monitor. The results are presented as counts/60 minutes, or counts/30 minutes, in arbitrary length units. Statistical comparisons are carried out using Student's t-test against the control group. In MK-801 or amphetamine pre-treated animals, statistical comparisons are made against the MK801 or d-amphetamine controls, respectively.

ED$_{50}$ values for reduction of amphetamine-induced hyperlocomotion are calculated by curve fitting. For most compounds, the evaluation is based on 16 amphetamine pre-treated animals over the dose range 0, 11, 33 and 100 μmol/kg s.c. in one single experiment, with complementary doses in separate experiments. Calculations are based on distance during the last 45 minutes of one hour of measurement. The distances are normalised to amphetamine-control and fitted by least square minimization to the function "End-(End-Control)/(1+(dose/ED$_{50}$)$^{Slope}$)". The four parameters (Control, End, ED$_{50}$ and Slope) are fitted with the restrictions: ED$_{50}$>0, 0.5<Slope<3, End=0% of control. The restriction with locked End is made to focus on potency rather than efficacy. To estimate confidence levels for the parameters, the fit is repeated 100 times with a random evenly distributed squared weight (0 to 1) for every measurement value. Presented ED$_{50}$-ranges cover 95% of these values.
In Vivo Test: Neurochemistry After the behavioural activity sessions, the rats are decapitated and their brains rapidly taken out and put on an ice-cold petri-dish. The limbic forebrain, the striatum, the frontal cortex and the remaining hemispheral parts of each rat are dissected and frozen. Each brain part is subsequently analyzed with respect to its content of monoamines and their metabolites.

The monoamine transmitter substances (NA (noradrenaline), DA (dopamine), 5-HT (serotonin)) as well as their amine (NM (normethanephrine), 3-MT (3-methoxytyramine)) and acid (DOPAC (3,4-dihydroxyphenylacetic acid), 5-HIAA (5-hydroxyindoleacetic acid), HVA (homovanillic acid)) metabolites are quantified in brain tissue homogenates by HPLC separations and electrochemical detection.

The analytical method is based on two chromatographic separations dedicated for amines or acids. Two chromatographic systems share a common auto injector with a 10-port valve and two sample loops for simultaneous injection on the two systems. Both systems are equipped with a reverse phase column (Luna C18(2), dp 3 μm, 50*2 mm i.d., Phenomenex) and electrochemical detection is accomplished at two potentials on glassy carbon electrodes (MF-1000, Bioanalytical Systems, Inc.). The column effluent is passed via a T-connection to the detection cell or to a waste outlet. This is accomplished by two solenoid valves, which block either the waste or detector outlet. By preventing the chromatographic front from reaching the detector, better detection conditions are achieved. The aqueous mobile phase (0.4 ml/min) for the acid system contains citric acid 14 mM, sodium citrate 10 mM, MeOH 15% (v/v) and EDTA 0.1 mM. Detection potentials relative to Ag/AgCl reference are 0.45 and 0.60V. The aqueous ion pairing mobile phase (0.5 ml/min) for the amine system contains citric acid 5 mM, sodium citrate 10 mM, MeOH 9% (v/v), MeCN 10.5% v/v), decane sulfonic acid 0.45 mM, and EDTA 0.1 mM. Detection potentials relative to Ag/AgCl reference are 0.45 and 0.65V.

ED$_{50}$ values for the increase of DOPAC in striatum are calculated by curve fitting. For most compounds, the evaluation is based on 20 animals over the dose range 0, 3.7, 11, 33 and 100 μmol/kg s.c. in one single experiment, with complementary doses in separate experiments. The DOPAC levels are normalised to control and fitted by least square minimization to the function "End-(End-Control)/(1+(dose/

$ED_{50})^{Slope})$". The four parameters (Control, End, $ED_{50}$ and Slope) are fitted with the restrictions: $ED_{50}>0$, $0.5<Slope<3$, $350<End<400\%$ of control. To estimate confidence levels for the parameters, the fit is repeated 100 times with a random evenly distributed squared weight (0 to 1) for every measurement value. Presented $ED_{50}$-ranges cover 95% of these values.

In Vivo Test: Oral Bioavailability

Experiments are performed 24 hours after implantation of arterial and venous catheters. Test compound is administered orally at 12.5 µmol/kg or intravenously at 5 µmol/kg using the venous catheters, n=3 per group. Arterial blood samples are then taken during six hours at 0, 3, 9, 27, 60, 120, 180, 240, 300 and, 360 minutes after administration of the test compound. The oral bioavailability is calculated as the ratio of the AUC (Area under curve) obtained after oral administration over the AUC obtained after intravenous administration for each rat. The parameter AUC is calculated according to the following:

AUC: the area under the plasma concentration versus time curve from time zero to the last concentration measured (Clast), calculated by the log/linear trapezoidal method.

The levels of test compound are measured by means of liquid chromatography-mass spectrometry (LC-MS) (Hewlett-Packard 1100MSD Series). The LC-MS module includes a quaternary pump system, vacuum degasser, thermostatted autosampler, thermostatted column compartment, diode array detector and API-ES spray chamber. Data handling was performed with a HP ChemStation rev.A.06.03. system. Instrument settings: MSD mode: Selected ion monitoring (SIM) MSD polarity: Positiv Gas temp: 350° C. Drying gas: 13.0 l/min Nebulizer gas: 50 psig Capillary voltage: 5000 V Fragmentor voltage: 70 V Analytical column: Zorbax eclipse XDB-C8 (4.6*150 mm, 5 µm) at 20° C. The mobile phase is acetic acid (0.03%) (solvent A) and acetonitrile (solvent B). The flow rate of the mobile phase is 0.8 ml/min. The elution is starting at 12% of solvent β isocratic for 4.5 min, then increasing linearity to 60% over 4.5 min.

Extractions procedure: Plasma samples (0.25-0.5 ml) are diluted with water to 1 ml, and 60 pmol (100 µl) internal standard (−)-OSU6241 is added. The pH is adjusted to 11 by the addition of 25 µl saturated $Na_2CO_3$. After mixing, the samples are extracted with 4 ml dichloromethane by shaking for 20 min. The organic layer is after centrifugation transferred to a smaller tube and evaporated to dryness under a stream of nitrogen. The residue is then dissolved in 120 µl mobile phase (acetic acid (0.03%): acetonitrile, 95:5) for LC-MS analysis (10 µl injected). The selective ion ($MH^+$) is monitored for each example, and $MH^+296$ for (−)-OSU6241 ((3-[3-(ethylsulfonyl)phenyl]-1-propylpiperidine).

A standard curve over the range of 1-500 pmol is prepared by adding appropriate amounts of test compound to blank plasma samples.

In Vitro Test: Metabolic Stability in Rat Liver Microsomes

Rat liver microsomes are isolated as described by Förlin [Förlin L: Effects of Clophen A50, 3-methylcholantrene, pregnenolone-16aq-carbonitrile and Phenobarbital on the hepatic microsomal cytochrome P-450-dependent monooxygenaser system in rainbow trout, salmo gairdneri, of different age and sex; Tox. Appl. Pharm. 1980 54 (3) 420-430] with minor modifications e.g. 3 mL/g liver of a 0.1 M Na/K*$PO_4$ buffer with 0.15M KCl, pH 7.4, (buffer 1) is added before homogenisation, the homogenate is centrifuged for 20 minutes instead of 15, the supernatant is ultracentrifuged at 100.000 g instead of 105.000 g and the pellet from the ultracentrifugation is resuspended in 1 mL/g liver of 20% v/v 87% glycerol in buffer 1.

1 µL of, 0.2 or 1 mM test substance diluted in water, and 10 µL 20 mg/mL rat liver microsome are mixed with 149 µL 37° C. buffer 1 and the reaction is started by addition of 40 µL 4.1 mg/mL NADPH. After 0 or 15 minutes incubation at 37° C. in a heating block (LAB-LINE, MULTI-BLOK Heater or lab4you, TS-100 Thermo shaker at 700 rpm) the reaction is stopped by addition of 100 µL pure acetonitrile. The protein precipitation is then removed by rejecting the pellet after centrifugation at 10.000 g for 10 minutes (Heraeus, Biofuge fresco) in 4° C. The test compound is analysed using HPLC-MS (Hewlett-Packard 1100MSD Series) with a Zorbax SB-C18 column (2.1*150 mm, 5 µm) using 0.03% formic acid and acetonitrile as mobile phase (gradient) or a Zorbax Eclipse XDB-C18 (3*75 mm, 3.5 µm) using 0.03% acetic acid and acetonitrile as mobile phase (gradient). The 15 min turnover is calculated as the fraction of test compound eliminated after 15 minutes, expressed in percent of 0 min levels, i.e. 100*[conc test compound at 0 min−concentration at 15 min]/conc at 0 min.

Preparation of liver microsomes is performed as described by Förlin [Förlin L: Effects of Clophen A50, 3-methylcholantrene, pregnenolone-16aq-carbonitrile and Phenobarbital on the hepatic microsomal cytochrome P-450-dependent monooxygenaser system in rainbow trout, salmo gairdneri, of different age and sex; Tox. Appl. Pharm. 1980 54 (3) 420-430]. Protocols for incubation with liver microsomes are referred in Crespi & Stresser [Crespi C L, Stresser D M: Fluorometric screening for metabolism based drug-drug interactions; J. Pharm. Tox. Meth. 2000 44 325-331], and Renwick et al. [Renwick et al.: Metabolism of 2,5-bis(trifluoromethyl)-7-benzyloxy-4-trifluoromethylcoumarin by human hepatic CYP isoforms: evidence for selectivity towards CYP3A4; Xenobiotica 2001 31 (4) 187-204].

Microdialysis

Male Sprague-Dawley rats weighing 220-320 g are used throughout the experiments. Before the experiment the animals are group housed, five animals in each cage, with free access to water and food. The animals are housed at least one week after arrival prior to surgery and use in the experiments. Each rat is used only once for microdialysis.

We use a modified version [see Waters N, Lofberg L, Haadsma-Svensson S, Svensson K, Sonesson C, Carlsson A: Differential effects of dopamine D2 and D3 receptor antagonists in regard to dopamine release, in vivo receptor displacement and behaviour; J. Neural. Transm. Gen. Sect. 1994 98 (1) 39-55] of the I-shaped probe described by Santiago & Westerink [Santiago M, Westerink B H C: Characterization of the in vivo release of dopamine as recorded by different types of intracerebral microdialysis probes; Naunyn-Schmiedeberg's Arch. Pharmacol. 1990 342 407-414]. The dialysis membrane we use is the AN69 polyacrylonitrile/sodium-methalylsulfonate copolymer (HOSPAL; o.d./i.d. 310/220 µm: Gambro, Lund, Sweden). In the dorsal striatum we use probes with an exposed length of 3 mm of dialysis membrane and in the prefrontal cortex the corresponding length is 2.5 mm. The rats are operated under isoflurane inhalationanesthesia while mounted into a Kopf stereotaxic instrument. Co-ordinates are calculated relative to bregma; dorsal striatum AP+1, ML±2.6, DV−6.3; Pf cortex, AP+3.2, 8° ML±1.2, DV−4.0 according to Paxinos & Watson [Paxinos G, Watson C: The Rat Brain in Stereotaxic Coordinates; New York, Academic Press, 1986]. The dialysis probe is positioned in a burr hole under stereotaxic guidance and cemented with phosphatine dental cement.

The rats are housed individually in cages for 48 h before the dialysis experiments, allowing them to recover from surgery and minimizing the risk of drug interactions with the anaesthetic during the following experiments. During this period the rats have free access to food and water. On the day of experiment the rats are connected to a micro perfusion pump via a swiwel and are replaced in the cage where they can move freely within its confinements. The perfusion medium is a Ringer's solution containing in mmol/l: NaCl; 140, CaCl2; 1.2, KCl; 3.0, MgCl2; 1.0 and ascorbic acid; 0.04 according to Moghaddam & Bunney [Moghaddam B, Bunney B S: Ionic Composition of Microdialysis Perfusing Solution Alters the Pharmacological Responsiveness and Basal Outflow of Striatal Dopamine; *J. Neurochem.* 1989 53 652-654]. The pump is set to a perfusion speed of 2 µl/min and 40 µl samples are collected every 20 min.

Each sample is analyzed at two HPLC systems. On an autoinjector (CMA 200) with a 10-port valve (Valco Cl OWE), holding two sample loops in series (4 µl and 20 µl), each brain dialysate sample is loaded in both loops simultaneously. At injection the 20 µl sample is introduced into a column switching system (reverse-phase combined with reverse-phase ion-pairing) for dopamine (DA), noradrenaline (NA), normetanephrine (NM), 3-methoxytyramine (3-MT) and serotonin (5-hydroxytryptamine, 5-HT) determination, while the 4 µl sample is introduced on a reverse-phase column for the chromatography of the acidic monoamine metabolites 3,4-di-hydroxyphenylacetic acid (DOPAC), homovanillic acid (HVA) and 5-hydroxyindoleacetic acid (5-HIAA). The currents generated by the two EC detectors are converted to digital data and evaluated using Chromeleon software (Dionex) on a PC. The method sample turn over time is 4.5 min and two parallel experiments are normally analyzed simultaneously on the system.

After the experiment the rats are uncoupled from the perfusion pump and decapitated. Their brains are rapidly taken out and fixed in Neo-fix solution (Kebo-lab, Sweden) for subsequent inspection of probe localisation. The Animal Ethics Committee in Göteborg, Sweden approved the procedures applied in these experiments.

The invention claimed is:
1. A compound of Formula 1:

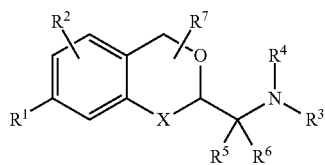

any of its stereoisomers or any mixture of its stereoisomers, or an N-oxide thereof, or a pharmaceutically acceptable salt thereof, wherein
X is O, S, NH or $CH_2$;
$R^1$ is selected from the group consisting of $OSO_2CF_3$, $OSO_2OH_3$, $NHSO_2CH_3$, $NHSO_2CF_3$, $SOR^8$, $SO_2R^8$, $SO_2NH_2$, $SO_2NHCH_3$, $SO_2N(CH_3)_2$, $COR^8$, $CSR^8$, CN, $OCF_3$, $SCF_3$, $OCHF_2$, $SCHF_2$, $CF_3$, F, Cl Br, I, $NO_2$, $SF_5$, SCN, OCN, $OCOCF_3$, $SCOCF_3$, $OCOCH_3$, $SCOCH_3$ and $CH(OH)CF_3$;
$R^2$ is selected from the group consisting of H, CN, F, Cl, Br, I and $CH_3$;
$R^3$ is selected from the group consisting of $C_1$-$C_5$ alkyl, allyl, $CH_2CH_2OCH_3$, $CH_2CH_2CH_2F$, $CH_2CH_2CHF_2$, $CH_2CH_2F$, 3,3,3-trifluoropropyl, 4,4,4-trifluorobutyl, $CH_2CH_2OH$, $CH_2CH_2CH_2OH$, $CH_2CH(OH)CH_3$, $CH_2CH_2COCH_3$, $C_3$-$C_6$ cycloalkyl,

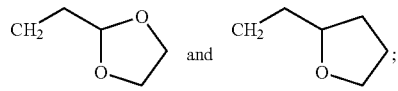

and $R^4$ is selected from the group consisting of H, $C_1$-$C_5$ alkyl, allyl, $CH_2CH_2OCH_3$, $CH_2CH_2CH_2F$, $CH_2CH_2CHF_2$, $CH_2CH_2F$, 3,3,3-trifluorpropyl, 4,4,4-trifluorobutyl, $CH_2CH_2OH$, $CH_2CH_2CH_2OH$, $CH_2CH(OH)CH_3$, $CH_2CH_2COCH_3$,

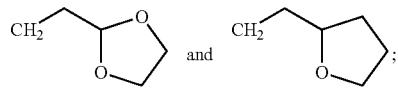

or $R^3$ and $R^4$ together with the nitrogen atom to which they are attached form a four- to six-membered heterocyclic ring, which heterocyclic ring may optionally comprise as a ring member, one oxygen atom, and/or one additional nitrogen atom; and which heterocyclic ring may optionally be substituted with $C_1$-$C_5$ alkyl; and $R^5$, $R^6$ and $R^7$ are selected from the group consisting of H and $CH_3$;

$R^8$ is selected from the group consisting of $C_1$-$C_3$ alkyl, $CF_3$, $CHF_2$, $CH_2F$ and CN.

2. The compound according to claim 1, any of its stereoisomers or any mixture of its stereoisomers, or an N-oxide thereof, or a pharmaceutically acceptable salt thereof, wherein X is O, S, NH or $CH_2$.

3. The compound according to claim 1, any of its stereoisomers or any mixture of its stereoisomers, or an N-oxide thereof, or a pharmaceutically acceptable salt thereof, wherein
$R^1$ is selected from the group consisting of $OSO_2CF_3$, $OSO_2CH_3$, $NHSO_2CH_3$, $NHSO_2CF_3$, $SOR^8$, $SO_2R^8$, $SO_2NH_2$, $SO_2NHCH_3$, $SO_2N(CH_3)_2$, $COR^8$, $CSR^8$, CN, $OCF_3$, $SCF_3$, $OCHF_2$, $SCHF_2$, $CF_3$, F, Cl, Br, I, $NO_2$, $SF_5$, SCN, OCN, $OCOCF_3$, $SCOCF_3$, $OCOCH_3$, $SCOCH_3$ and $CH(OH)CF_3$; and
$R^8$ is selected from the group consisting of $C_1$-$C_3$ alkyl, $CF_3$, $CH_2F$ and CN.

4. The compound according to claim 1, any of its stereoisomers or any mixture of its stereoisomers, or an N-oxide thereof, or a pharmaceutically acceptable salt thereof, wherein $R^2$ is selected from the group consisting of H, CN, F, Cl, I and $CH_3$.

5. The compound according to claim 1, any of its stereoisomers or any mixture of its stereoisomers, or an N-oxide thereof, or a pharmaceutically acceptable salt thereof, wherein $R^3$ is selected from the group consisting of $C_1$-$C_5$ alkyl, allyl, $CH_2CH_2OCH_3$, $CH_2CH_2CH_2F$, $CH_2CH_2CHF_2$, $CH_2CH_2F$, 3,3,3-trifluoropropyl, 4,4,4-trifluorobutyl, $CH_2CH_2OH$, $CH_2CH_2CH_2OH$, $CH_2CH(OH)CH_3$, $CH_2CH_2COCH_3$, $C_3$-$C_6$cycloalkyl,

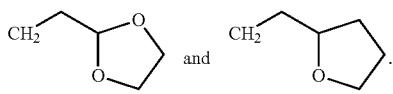

6. The compound according to claim 1, any of its stereoisomers or any mixture of its stereoisomers, or an N-oxide thereof, or a pharmaceutically acceptable salt thereof, wherein $R^4$ is selected from the group consisting of H, $C_1$-$C_5$alkyl, allyl, $CH_2CH_2OCH_3$, $CH_2CH_2CH_2F$, $CH_2CH_2CHF_2$, $CH_2CH_2F$, 3,3,3-trifluoropropyl, 4,4,4-trifluorobutyl, $CH_2CH_2OH$, $CH_2CH_2CH_2OH$, $CH_2CH(OH)CH_3$, $CH_2CH_2COCH_3$,

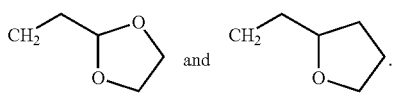

7. The compound according to claim 1, any of its stereoisomers or any mixture of its stereoisomers, or an N-oxide thereof, or a pharmaceutically acceptable salt thereof, wherein $R^3$ and $R^4$ together with the nitrogen atom to which they are attached form a four- to six-membered heterocyclic ring, which heterocyclic ring may optionally comprise as a ring member, one oxygen atom, and/or one additional nitrogen atom; and which heterocyclic ring may optionally be substituted with $C_1$-$C_5$ alkyl.

8. The compound according to claim 1, any of its stereoisomers or any mixture of its stereoisomers, or an N-oxide thereof, or a pharmaceutically acceptable salt thereof, wherein $R^5$, $R^6$ and $R^7$ are selected from the group consisting of H and $CH_3$.

9. The compound according to claim 1, which is
N-{[7-(TRIFLUOROMETHYL)-4H-1,3-BENZO-DIOXIN-2-YL]METHYL}PROPAN-1-AMIN;
1-{[7-(METHYLSULFONYL)-4H-1,3-BENZO-DIOXIN-2-YL]METHYL}PYRROLIDINE;
N-{[7-(METHYLSULFONYL)-4H-1,3-BENZO-DIOXIN-2-YL]METHYL}PROPAN-1-AMINE;
(−)-N-{[7-(METHYLSULFONYL)-4H-1,3-BENZO-DIOXIN-2-YL]METHYL}PROPAN-1-AMINE;
(+)-N-{[7-(METHYLSULFONYL)-4-1,3-BENZO-DIOXIN-2-YL]METHYL}PROPAN-1-AMINE;
N-{[7-(METHYLSULFONYL)-4H-1,3-BENZO-DIOXIN-2-YL]METHYL}PROPAN-2-AMINE;
1-({7-[(TRIFLUOROMETHYL)SULFONYL]-4H-1,3-BENZODIOXIN-2-YL}METHYL)PYROLIDINE;
N-({7-[(TRIFLUOROMETHYL)SULFONYL]-4H-1,3-BENZODIOXIN-2-YL}METHYL)PROPAN-1-AMINE;
N-{[7-(METHYLSULFONYL)-4H-1,3BENZO-DIOXIN-2-YL]METHYL}ETHANAMINE;
(−)-N-{[7-(METHYLSULFONYL)-4H-1,3-BENZO-DIOXIN-2-YL]METHYL}ETHANAMINE;
(+)-N-{[7-(METHYLSULFONYL)-4H-1,3-BENZO-DIOXIN-2-YL]METHYL}ETHANAMINE;
N-METHYL-1-[7-(METHYLSULFONYL)-4H-1,3BENZODOXIN-2-YL]METHANAMINE;
(−)-N-METHYL-1-[7-(METHYLSULFONYL)-4H-1,3-BENZODIOXIN-2-YL]METHANAMINE;
(+)-N-METHYL-1-[7-(METHYLSULFONYL)-4H-1,3-BENZODIOXIN-2-YL]MET ANAMINE;
N-({7-[(TRIFLUOROMETHYL)SULFONYL]-4H-1,3-BENZODIOXIN-2-YL}METHYL)ETHANAMINE;
N-[(7-BROMO-5-FLUORO-4H-1,3-BENZODIOXIN-2-YL)METHYL]PROPAN-1-AMINE;
N-{[5-FLUORO-7-(METHYLSULFONYL)-4H-1,3-BENZODIOXIN-2-YL]METHYL}PROPAN-1-AMIME;
1-[5-FLUORO-7-(METHYLSULFONYL)-4H-1,3-BENZODIOXIN-2-YL]-N-METHYLMETHANAMINE;
N-[(7-BROMO-6-FLUORO-4H-1,3-BENZODIOXIN-2-YL)METHYL]PROPAN-1-AMINE;
N-{[6-FLUORO-7-(METHYLSULFONYL)-4H-1,3-BENZODIOXIN-2-YL]METHYL}PROPAN-1-AMINE;
1-{[7-(METHYLSULFONYL)-4H-1,3-BENZO-DIOXIN-2-YL]METHYL}PIPERIDINE;
N-{[7-(METHYLSULONYL)-4H-1,3-BENZODIOXIN-2-YL]METHYL}BUTAN-1-AMINE;
2-({[7-(METHYLSULFONYL)-4H-1,3-BENZO-DIOXIN-2-YL]METHYL}AMINO)ETHANOL;
N-{[7-(METHYLSULFONYL)-4H-1,3-BENZO-DIOXIN-2-YL]METHYL}-N,N-PROPYLPROPAN-1-AMINE;
N-ETHYL-N-{[7-(METHYLSULFONYL)-4H-1,3-BENZODIOXIN-2-YL]METHYL}-N-PROPAN-1-AMINE;
N-{[7-(METHYLSULFONYL)-4H-1,3-BENZO-DIOXIN-2-YL]METHYL}PROP-2-EN-1-AMINE;
N,N-DIMETHYL-1-[7-(METHYLSUFONYL)-4H-1,3-BENZODOXIN-2-YL]METHANAMINE;
N-METHYL-N-{[7-(METHYLSULFONYL)-4H-1,3-BENZODIOXIN-2-YL]METHYL}PROPAN-1-AMINE;
1-{[7-(METHYLSULFONYL)-4H-1,3-BENZO-DIOXIN-2-YL]METHYL}AZETIDINE;
4-{[7-(METHYLSULFONYL)-4H-1,3-BENZO-DIOXIN-2-YL]METHYL}MORPHOLINE;2-METHOXY-N-{[7-(METHYLSULFONYL)-4H-1,3-BENZODIOXIN-2-YL]METHYL}ETHANAMINE;
N-ETHYL-N-{[7-(METHYLSULFONYL)-4H-1,3-BENZODIOXIN-2-YL]METHYL}ETHANAMINE;
N-METHYL-N-{[7(METHYLSULFONYL)-4H-1,3-BENZODIOXIN-2-YL]METHYL}ETHANAMINE;
N-{[5-FLUORO-7-(METHYLSULFONYL)-4H-1,3BENZODIOXIN-2-YL]METHYL}ETHANAMINE;
1-{[5-FLUORO-7-(METHYLSULFONYL)-4H-1,3-BENZODIOXIN-2-YL]METHYL}PIPERIDINE;
N-{[5-FLUORO-7-(METHYLSULFONYL)-4H-1,3-BENZODIOXIN-2-YL]METHYL}-2-METHYLPROPAN-1-AMINE;
N-{[5-FLUORO-7-(METHYLSULFONYL)-4H-1,3-BENZODIOXIN-2-YL]METHYL}BUTAN-1-AMINE;
1-{[5-FLUORO-7-(METHYLSULFONYL)-4H-1,3-BENZODIOXIN-2-YL]METHYL}PYRROLIDINE;
N-{[5-FLUORO-7-(METHYLSULFONYL)-4H-1,3-BENZODIOXIN-2-YL]METHYL}PROP-2-EN-1-AMINE;
N-{[5-FLUORO-7-(METHYLSULFONYL)4H-1,3-BENZODIOXIN-2-YL]METHYL}-N-PROPYLPROPAN-1-AMINE;
1-[5-FLUORO-7-(METHYLSULFONYL)-4H-1,3-BENZODIOXIN-2YL]-N,N -DIMETHYLMETHANAMINE;
N-ETHYL-N-{[5-FLUORO-7-(METHYLSULFONYL)-4H-1,3-BENZODIOXIN-2-YL]METHYL}ETHANAMINE;

N-{[5-FLUORO-7(METHYLSULFONYL)-4H-1,3-BENZODIOXIN-2-YL]METHYL}PROPAN-2-AMINE;

N-{[5-FLUORO-7-(METHYLSULFONYL)-4H-1,3-BENZODIOXIN-2-YL]METHYL}-N-METHYL-PROPAN-1-AMINE;

N-ETHYL-N-{[5-FLUORO-7-(METHYLSULFONYL)-4H-1,3-BENZODIOXIN-2-YL]METHYL}PROPAN-1-AMINE;

N-{[5-FLUORO-7(METHYLSULFONYL)-4H-1,3-BENZODIOXIN-2-YL]METHYL}-N-METHYL-ETHANAMINE;

N-{[5-FLUORO-7-(METHYLSULFONYL)-4H-1,3-BENZODIOXIN-2-YL]METHYL}2-METHOXY-ETHANAMINE;

1-{[5-FLUORO-7-(METHYLSULFONYL)-4H-1,3-BENZODIOXIN-2-YL]METHYL}AZETIDINE;

N-{[5-FLUORO-7-(METHYLSULFONYL)-4H-1,3-BENZODIOXIN-2-YL]METHYL}-2,2-DIMETHYL-PROPAN-1AMINE; or

3-FLUORO-N-{[5-FLUORO-7(METHYLSULFONYL)-4H-1,3-BENZODIOXIN-2-YL]METHYL}PROPAN-1-AMINE;

any of its stereoisomers or any mixture of its stereoisomers, or an N-oxide thereof, or a pharmaceutically acceptable salt thereof.

10. A pharmaceutical composition, comprising a therapeutically effective amount of a compound of claim 1, any of its stereoisomers or any mixture of its stereoisomers, or an N-oxide thereof, or a pharmaceutically acceptable salt thereof, together with at least one pharmaceutically acceptable carrier, excipient or diluent.

11. A compound according to claim 1, any of its stereoisomers or any mixture of its stereoisomers, or an N-oxide thereof, or a pharmaceutically acceptable salt thereof, for use as a medicament.

12. A compound according to claim 1, any of its stereoisomers or any mixture of its stereoisomers, or an N-oxide thereof, or a pharmaceutically acceptable salt thereof, for use in the treatment or alleviation of a disease or a disorder or a condition of a mammal, including a human, which disease, disorder or condition is responsive to modulation of dopaminergic function in the central nervous system.

* * * * *